(12) United States Patent
Wilkinson

(10) Patent No.: US 8,048,096 B2
(45) Date of Patent: Nov. 1, 2011

(54) LANCET DEVICE

(75) Inventor: Bradley Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1102 days.

(21) Appl. No.: 11/270,330

(22) Filed: Nov. 9, 2005

(65) Prior Publication Data

US 2006/0129173 A1    Jun. 15, 2006

Related U.S. Application Data

(63) Continuation of application No. 11/123,849, filed on May 6, 2005.

(60) Provisional application No. 60/631,795, filed on Nov. 30, 2004, provisional application No. 60/631,846, filed on Nov. 30, 2004.

(51) Int. Cl.
  *A61B 17/32* (2006.01)
(52) U.S. Cl. .......................... 606/181; 606/182
(58) Field of Classification Search .......... 606/181–183; D24/146, 147; 604/136, 157
  See application file for complete search history.

(56) References Cited

U.S. PATENT DOCUMENTS

| | | |
|---|---|---|
| 3,741,197 A | 6/1973 | Sanz |
| 4,577,630 A | 3/1986 | Nitzsche et al. |
| 4,637,403 A | 1/1987 | Garcia et al. |
| 4,653,513 A | 3/1987 | Dombrowski et al. |
| D299,748 S | 2/1989 | Robertson |
| 4,817,603 A | 4/1989 | Turner et al. |
| 4,869,249 A | 9/1989 | Crossman et al. |
| 5,100,427 A | 3/1992 | Crossman et al. |
| 5,314,441 A | 5/1994 | Cusack et al. |
| 5,366,470 A | 11/1994 | Ramel |
| 5,439,473 A | 8/1995 | Jorgensen |
| 5,540,709 A | 7/1996 | Ramel |
| 5,554,166 A | 9/1996 | Lange et al. |
| 5,611,809 A | 3/1997 | Marshall et al. |
| 5,628,765 A | 5/1997 | Morita |
| 5,643,306 A | 7/1997 | Schraga |

(Continued)

FOREIGN PATENT DOCUMENTS

EP    0569124    11/1993

(Continued)

OTHER PUBLICATIONS

U.S. Appl. No. 11/123,849, filed May 6, 2005.

(Continued)

*Primary Examiner* — Corrine M McDermott
*Assistant Examiner* — Melissa Ryckman
(74) *Attorney, Agent, or Firm* — The Webb Law Firm

(57) ABSTRACT

A lancet device generally includes a housing having opposing lateral sides extending between a forward end and a rearward end, and a shield coaxially and movably associated with the housing. The housing includes a plurality of longitudinal ribs extending along a portion of at least one of the opposing lateral sides. The plurality of longitudinal ribs form a finger grip on at least one of, and typically both of the opposing lateral sides. The shield is generally movable from a first position in which the shield extends outwardly from the forward end of the housing to a second position in which the shield is at least partially moved within the housing, based on axial pressure applied by the user against the finger grip formed by the longitudinal ribs.

29 Claims, 32 Drawing Sheets

U.S. PATENT DOCUMENTS

| | | | |
|---|---|---|---|
| D387,865 S | * | 12/1997 | Peckham et al. ............. D24/146 |
| 5,707,384 A | | 1/1998 | Kim |
| 5,755,733 A | | 5/1998 | Morita |
| 5,908,434 A | | 6/1999 | Schraga |
| 5,957,895 A | | 9/1999 | Sage et al. |
| 6,090,124 A | | 7/2000 | Weekes |
| 6,168,606 B1 | | 1/2001 | Levin |
| 6,248,120 B1 | | 6/2001 | Wyszogrodzki |
| D444,557 S | | 7/2001 | Levaughn et al. |
| 6,258,112 B1 | | 7/2001 | Schraga |
| D447,566 S | | 9/2001 | Levaughn et al. |
| 6,283,982 B1 | | 9/2001 | Levaughn et al. |
| 6,299,626 B1 | | 10/2001 | Viranyi |
| 6,322,574 B1 | | 11/2001 | Lloyd et al. |
| 6,432,120 B1 | | 8/2002 | Teo |
| 6,491,709 B2 | | 12/2002 | Sharma et al. |
| 6,514,270 B1 | | 2/2003 | Schraga |
| 6,613,064 B2 | | 9/2003 | Rutynowski et al. |
| D499,182 S | | 11/2004 | Moore et al. |
| 2001/0039387 A1 | | 11/2001 | Rutynowski et al. |
| 2002/0040230 A1 | | 4/2002 | Kuhr |
| 2002/0082521 A1 | | 6/2002 | Sharma |
| 2002/0128608 A1 | | 9/2002 | Teo et al. |
| 2003/0109895 A1 | | 6/2003 | Taylor et al. |
| 2003/0199891 A1 | | 10/2003 | Argauer |
| 2004/0133172 A1 | | 7/2004 | Wilkinson |
| 2005/0159768 A1 | * | 7/2005 | Boehm et al. ................. 606/182 |

FOREIGN PATENT DOCUMENTS

| | | |
|---|---|---|
| EP | 0 747 006 A | 12/1996 |
| NL | 7117611 | 6/1972 |
| NL | 7117611 A | 6/1972 |
| WO | WO 03/049613 | 6/2003 |
| WO | WO 03/049613 A | 6/2003 |
| WO | WO 03/092512 A | 11/2003 |
| WO | WO 2005/110227 | 5/2005 |
| WO | 2005110227 A | 11/2005 |

OTHER PUBLICATIONS

U.S. Appl. No. 29/219,599, filed Dec. 17, 2004.

U.S. Appl. No. 29/219,598, filed Dec. 17, 2004.

* cited by examiner

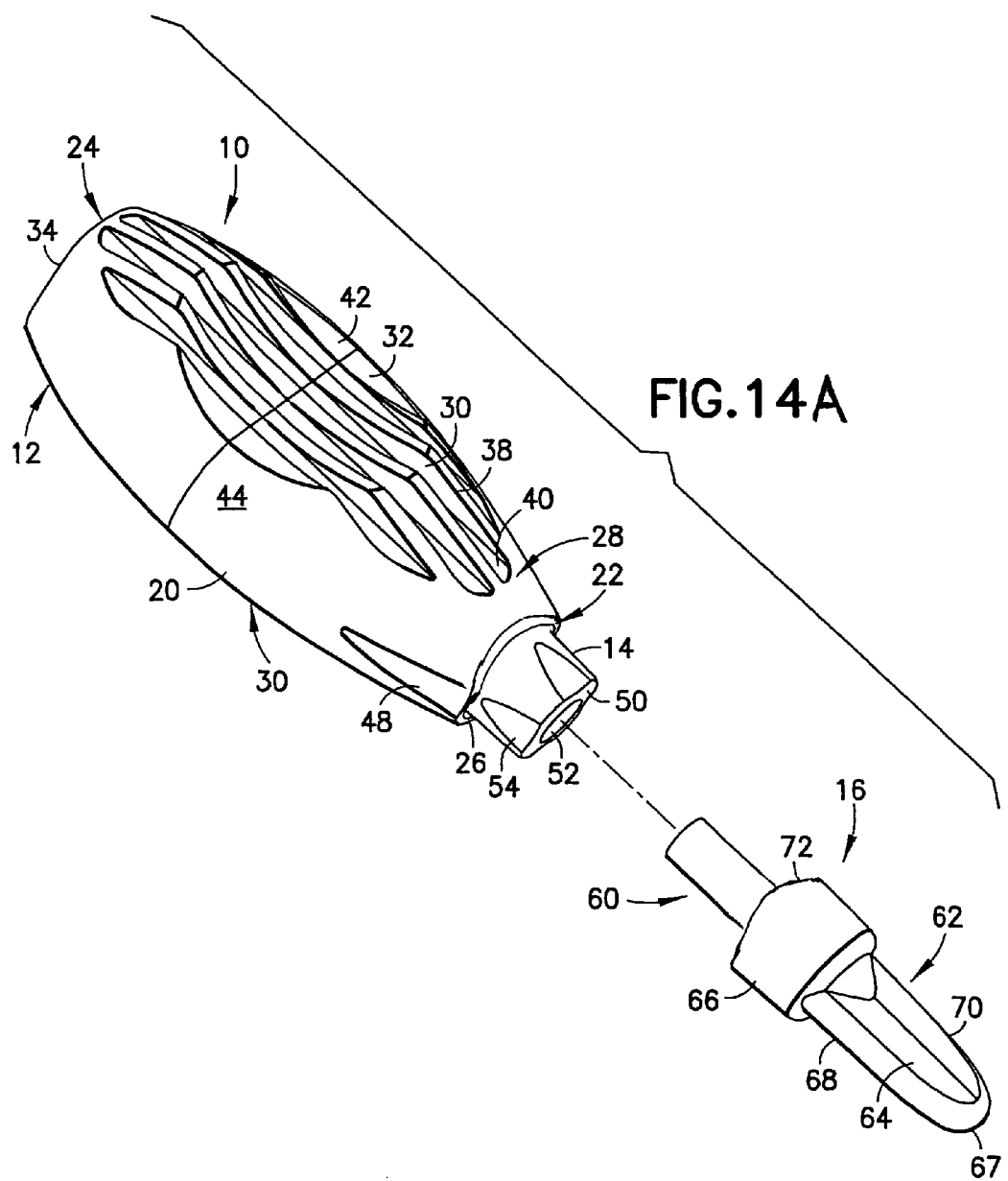

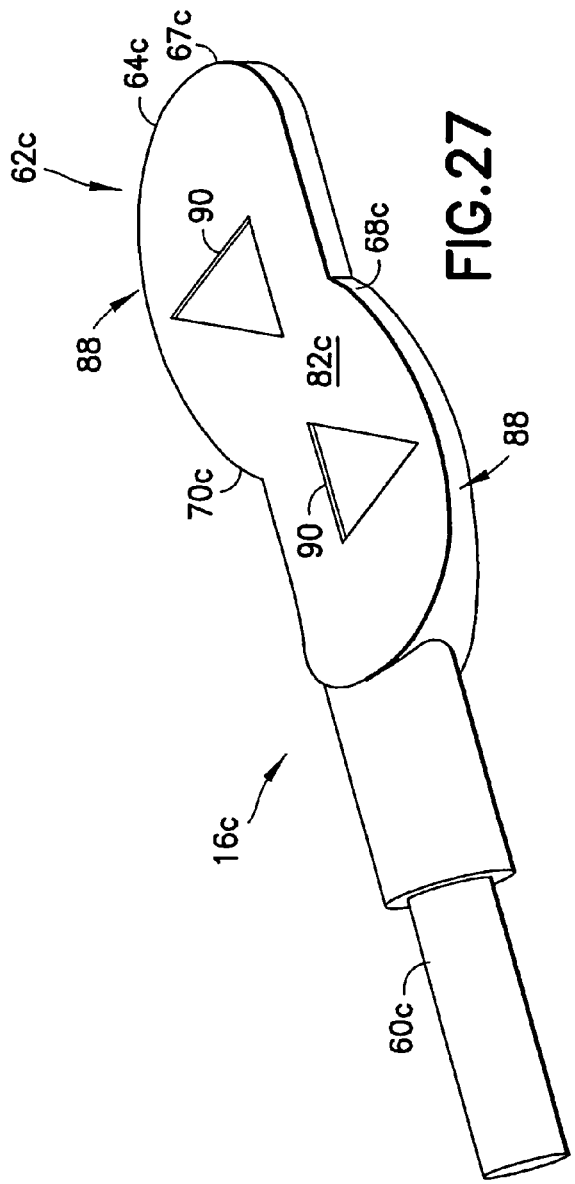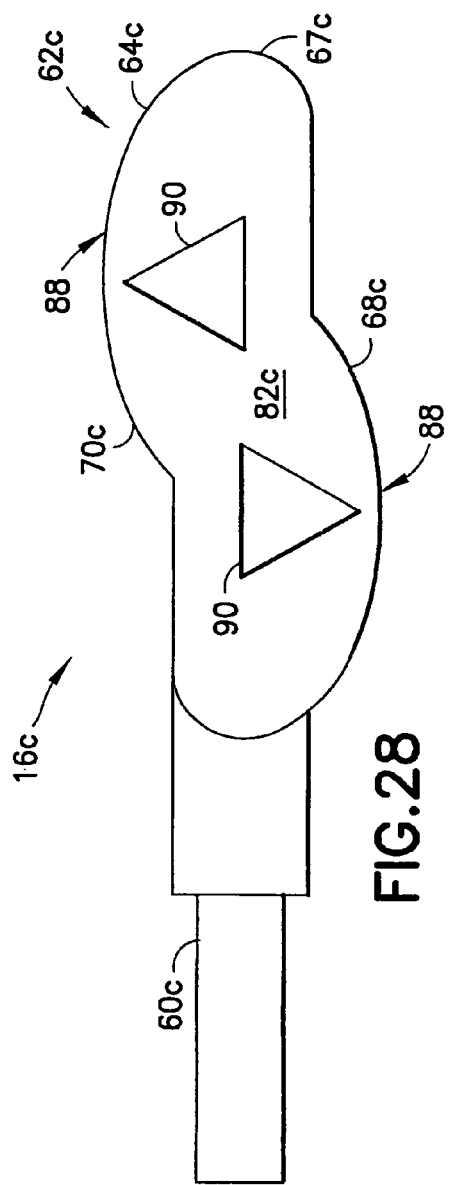

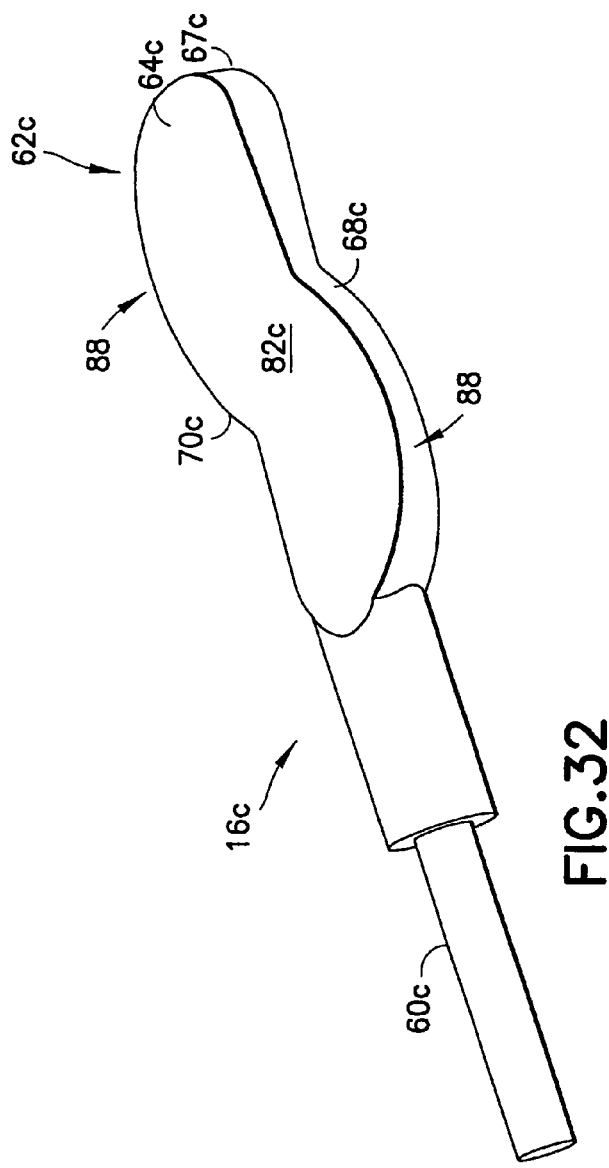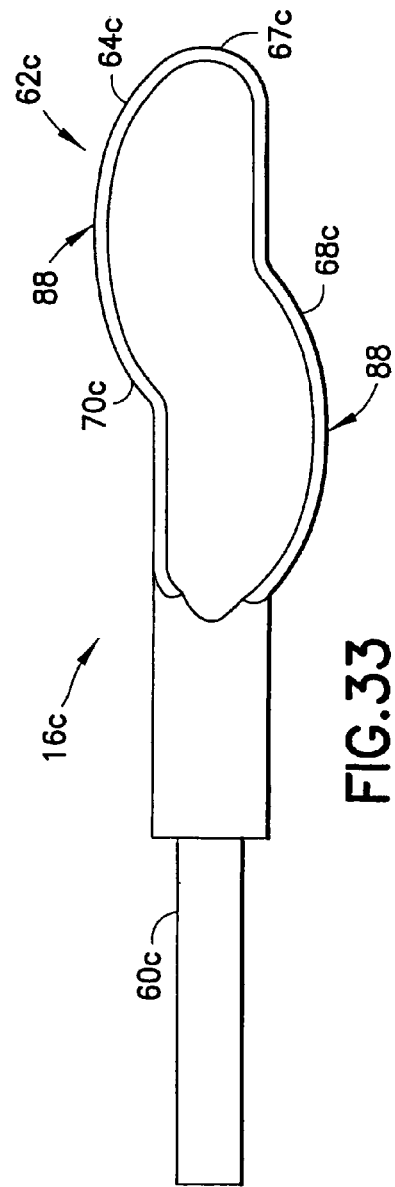

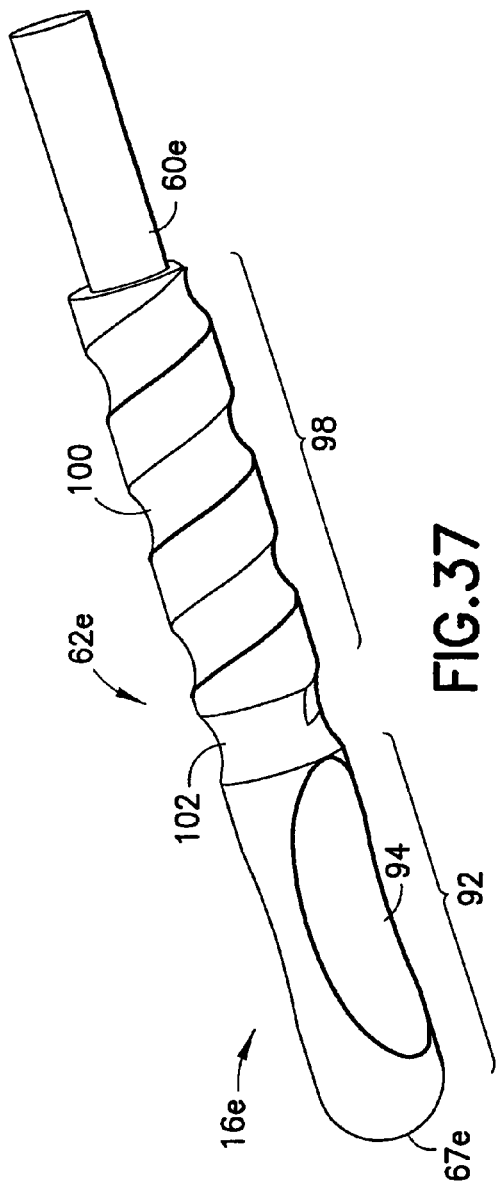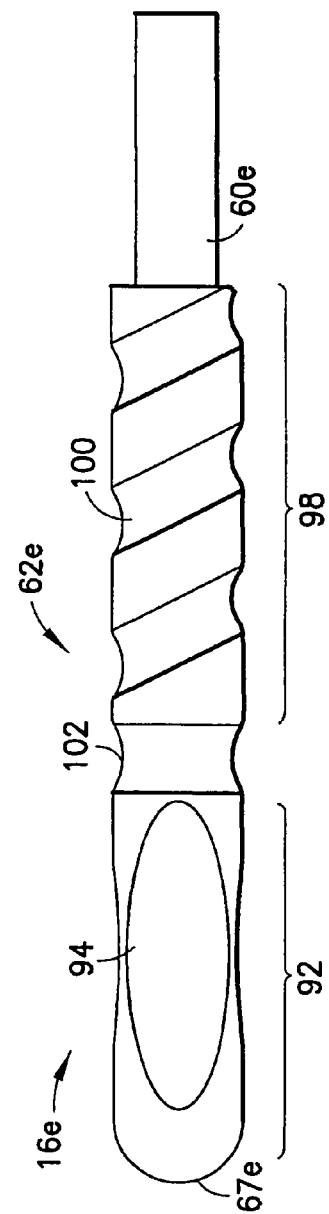

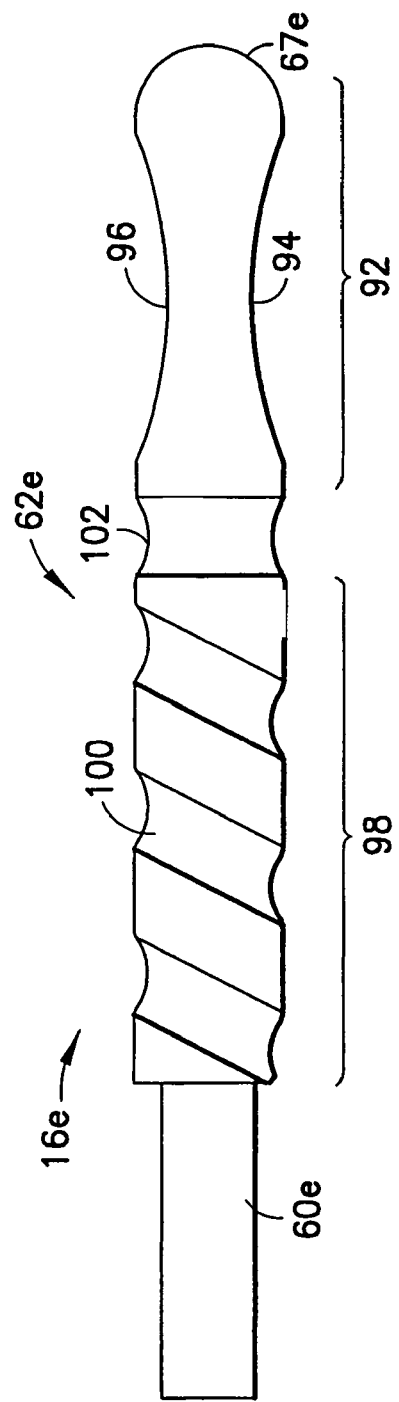
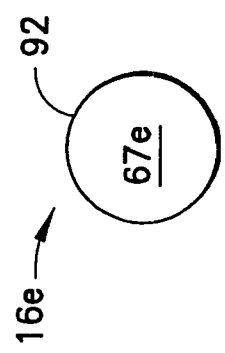
FIG. 39
FIG. 40

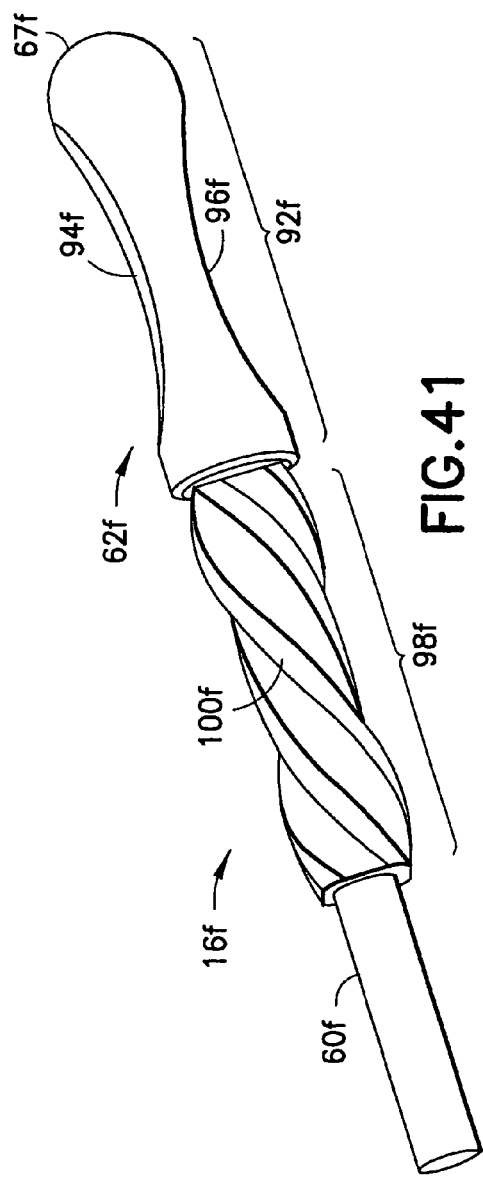
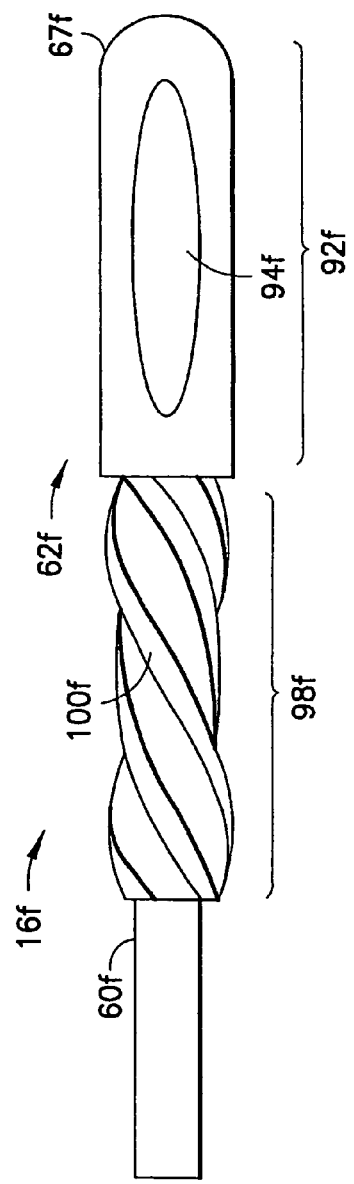
FIG. 41
FIG. 42

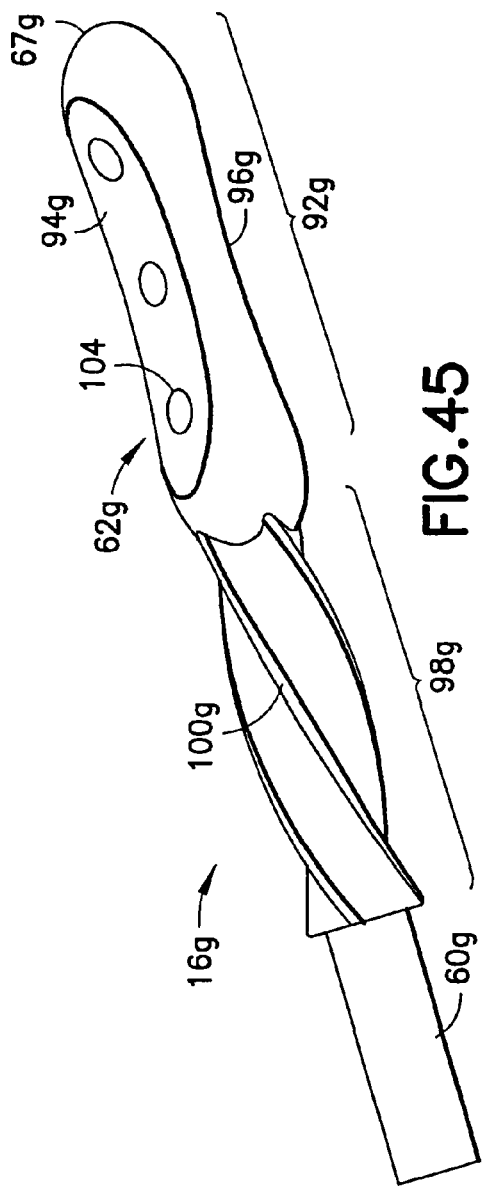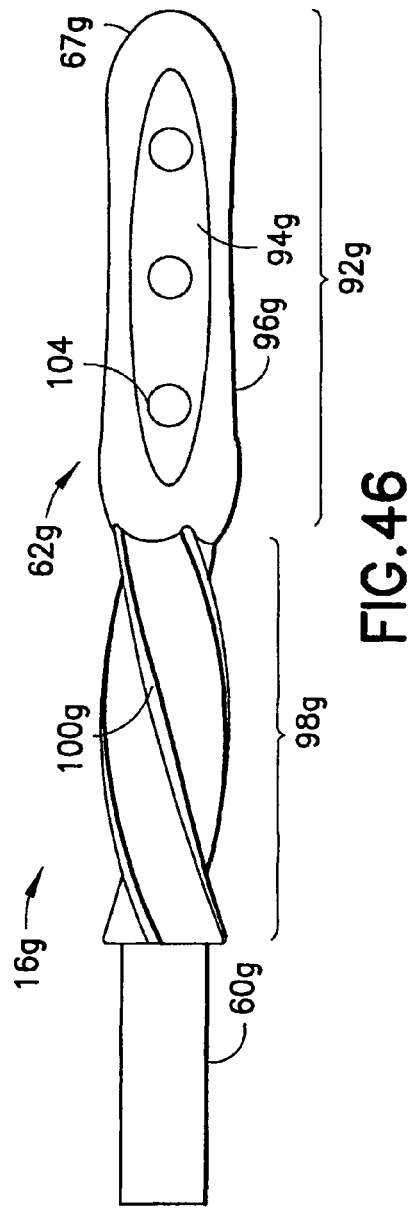

LANCET DEVICE

The present application claims priority to U.S. Application No. 60/631,846 filed Nov. 30, 2004, U.S. Application No. 60/631,795 filed Nov. 30, 2004, and U.S. application Ser. No. 11/123,849 filed May 6, 2005.

BACKGROUND OF THE INVENTION

1. Field of the Invention

The present invention relates generally to medical puncturing devices, commonly referred to as lancets, which are used to take blood samples from patients and, more specifically, to a lancet device that is ergonomically designed for ease of use and manipulation by a user.

2. Description of Related Art

Lancet devices are used in the medical field for puncturing the skin of a patient to obtain a capillary blood sample from the patient. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests.

Various lancet devices are commercially available to hospitals, clinics, doctors' offices, and the like, as well as to individual consumers. Such devices typically include a sharp-pointed member such as a needle, or a sharp-edged member such as a blade, that is used to make a quick puncture wound or incision in the patient's skin in order to provide a small outflow of blood. It is often physiologically and psychologically difficult for many people to prick their own finger with a hand-held needle or blade. As a result, lancet devices have evolved into automatic devices that puncture or cut the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example on the finger. Often, a spring is incorporated into the device to provide the sufficient force necessary to puncture or cut the skin of the patient.

It is of the utmost importance in the medical field that such medical puncturing devices or lancets are in a sterile condition before use. Today, generally without exception, medical puncturing devices or lancets are manufactured and packaged in a sterilized condition before they are distributed to medical professionals and members of the public who have a need for such devices. The sterile packaging maintains the sterility of the device, ensuring that the surrounding environment does not contaminate it until use. In addition, it is also of increasing importance that the user or another person does not come into contact with the needle or blade after use of the device. With the concern over blood-borne diseases, medical professionals are required to take great care with medical devices that come into contact with the blood of patients. Thus, an important aspect of lancet design is concerned with preventing the needle or blade of the device from wounding the user or another person after the blood sample is drawn from the patient. Once used, the needle or blade should be shielded to prevent the needle or blade from wounding the user or another person handling the device. Moreover, the lancet device should be disposable to eliminate the chances of disease transmission due to the needle or blade being used on more than one person. In this regard, the lancet device should ideally be designed for one firing, and have safety features to prevent reuse.

Advances have been made in recent years to increase safety in operating and handling used lancet devices. For example, lancet devices are currently available which are single shot devices that feature automatic ejection and retraction of the puncturing or cutting element from and into the device. Examples of such medical puncturing devices are disclosed in U.S. Pat. Nos. 6,432,120; 6,248,120; 5,755,733; and 5,540,709.

U.S. Pat. No. 6,432,120 to Teo discloses a lancet device that includes a lancet holder, which contains a spring-loaded lancet structure. The spring-loaded lancet structure includes a single spring that affects the ejection and retraction of a lancet needle upon the triggering of the structure. U.S. Pat. No. 6,248,120 to Wyszogrodzki discloses a lancet device comprised of a housing, a shielding portion, a piston with a puncturing tip, and drive and return springs that eject and retract the piston, respectively, upon the breakage of internal wing elements in the housing. U.S. Pat. No. 5,755,733 to Morita discloses a lancet device that includes a combined holder and lancet structure. The lancet structure includes a lancet member with a puncturing tip and a compressible spring member that causes the lancet member to puncture the skin of a patient upon actuation of a pair of actuating arms.

U.S. Pat. No. 5,540,709 to Ramel discloses a lancet device that includes a housing enclosing a slidable trigger, which is used to trigger a compressed spring that powers a piercing lancet member to pierce the skin of a patient. The housing includes a pair of internal fingers that engage the body of the lancet member, which are then released of engagement with the lancet member body by axial force applied by the user to the slidable trigger. Other medical puncturing devices or lancets known in the art are disclosed in U.S. Pat. Nos. 4,869,249 and 4,817,603. The devices disclosed in these references include a cap that is used to protect a needle or to keep the needle sterile.

Another important consideration in lancet design is to enable the user to easily manipulate the device with his or her fingertips. The lancet device is ideally easily held between the user's fingertips so that the user has control over the lancet device during a skin puncturing procedure. Typical lancet devices available in the marketplace are not designed for ease of use by the operator. In some designs, for example, the housing of the lancet device is simply a rectangular-shaped box that cooperates with a rectangular-shaped shield portion. In the foregoing design, the user is not provided surfaces for grasping the device with his or her fingertips. Additionally, the shape of the shield portion does not lend itself to instructing the user as to where the puncturing element will be discharged from the device to puncture the skin of the patient. The user must make a guess as to the approximate discharge location of the puncturing element when the shield portion is placed against the patient's skin. Generally, the lancet designs available in the marketplace are not user-friendly and a significant need is present in this area of lancet design.

SUMMARY OF THE INVENTION

In view of the foregoing, a need generally exists in the medical field for a medical puncturing device that is easy for a user to manipulate and use while ensuring sterility before use and safe and secure disposal after use. Additionally, a need exists in the medical field for a simple, inexpensive, reliable, self-activating, and disposable medical puncturing device for use in collecting blood samples.

An embodiment of the present invention provides a lancet device that generally includes a housing comprising opposing lateral sides extending between a forward end and a rearward end, with a plurality of longitudinal ribs extending along a portion of at least one of, and typically both of, the opposing lateral sides. The plurality of longitudinal ribs form a finger grip on one or both of the opposing lateral sides. A shield is coaxially and movably associated with the housing. Axial pressure applied by the user against the finger grip moves the housing and the shield with respect to each other from a first position in which the shield extends outwardly from the forward end of the housing to a second position in which the shield is at least partially moved within the housing.

The longitudinal ribs may extend along a portion of both of the opposing lateral sides of the housing forming finger grips on both of the opposing lateral sides. Further, a portion of each of the longitudinal ribs may be contoured to form the finger grip as a generally concave surface, while another portion of the longitudinal ribs may be contoured to form a generally convex surface. In one embodiment, the longitudinal ribs are contoured to generally form a forward convex surface at a portion of the opposing lateral side adjacent the forward end and a rearward convex surface at a portion of the opposing lateral side adjacent the rearward end of the housing, with a generally concave surface formed between the forward and the rearward convex surfaces. In such an embodiment, the longitudinal ribs forming the forward and the rearward convex surfaces may be aligned through the concave surface to form the finger grip as an indentation on at least of the opposing lateral sides of the housing. Also, in such an embodiment, the longitudinal ribs may form a generally oval concave surface.

The housing may also include a finger grip indentation formed on the rearward end of the housing for accommodating a user's finger during use of the lancet device, such as a concave indentation. Further, the shield may define a plurality of peripherally spaced indentations for visually indicating an alignment position of a puncturing element disposed within the housing and/or the shield.

In a further embodiment, a lancet device includes a housing extending between a forward end and a rearward end, with a shield extending coaxially through the forward end of the housing and movably associated with the housing, and a lancet assembly disposed in the housing and adapted to extend through an opening in a forward end of the shield upon movement of the shield with respect to the housing. Such a lancet device further includes a removable tab member having an inner portion maintaining sterility of a lance tip of the lancet assembly, and an outer portion enclosing the opening in the forward end of the shield and adapted to maintain the shield and the housing from axially moving with respect to each other.

The inner portion of the tab member may include a post substantially enclosing the lance tip, and the outer portion of the tab member may further include a grip portion adapted to be grasped by the user. The outer portion of the tab member may also include a depending skirt formed to engage an external surface of the forward end of the shield extending from the forward end of the housing.

The grip portion may further include a paddle-shaped member for grasping by the user. The paddle-shaped member may have opposed longitudinal edges that are oppositely curved, such that opposed sides of the paddle-shaped member define a contour to indicate to a user a rotational direction for rotating the tab member to assist in removing the tab member from the lance tip. A transverse cross-section through the paddle-shaped member may define a generally oval shape. However, the paddle-shaped member may define other symmetrical transverse cross-sectional shapes such as circular or polygonal, or have a nonsymmetrical transverse cross-sectional shape. The opposed sides of the paddle-shaped member may be concave, and may include at least one raised grip tab thereon.

The paddle-shaped member may define opposed longitudinal curved portions. The opposed longitudinal curved portions may be generally elliptical shaped. The paddle-shaped member may define at least one shaped indentation defined in at least one side thereof. The shaped indentation may be generally circular, oval, or polygonal shaped.

The grip portion of the tab member may define opposed finger grip indentations for grasping by the user. The grip portion finger grip indentations may be concave. The grip portion of the tab member may have an intermediate portion that defines a helical texture. The finger grip indentations may each include at least one raised grip tab. Further, the grip portion of the tab member may be detachable from the post.

The at least one finger grip indentation may comprise a concave surface shape facing substantially transversely away from an axis passing axially through the lancet assembly. The concave surface shape may be a semicircular, elliptical, hyperbolic or parabolic shape.

The sterile tab member may further be removably associated with the shield and engage a forward end of the shield and/or the housing to prevent movement of the shield relative to the housing that would cause the internal actuating mechanism to project the lancet assembly to a puncturing position. For example, a depending hollow skirt may at least partially encompass the shield and engage the housing distal end to prevent movement of the shield with respect to the housing. The skirt may be adapted to fully enclose the shield therein, and the shield may be frictionally held within the skirt.

Further details and advantages of the present invention will become apparent from the following detailed description when read in conjunction with the accompanying drawings.

BRIEF DESCRIPTION OF THE DRAWINGS

FIG. 14A is an exploded perspective view of a lancet device shown in an alternate embodiment, showing the tab member and the forward surface of the housing including corresponding cam-like engaging surfaces to facilitate separation of the tab member from the body of the lancet device;

FIG. 27 is a perspective view of a fourth embodiment of the tab member;

FIG. 28 is a plan view of the tab member of FIG. 27;

FIG. 32 is a perspective view of a fifth embodiment of the tab member;

FIG. 33 is a plan view of the tab member of FIG. 32;

FIG. 37 is a perspective view of a sixth embodiment of the tab member;

FIG. 38 is a plan view of the tab member of FIG. 37;

FIG. 39 is a side elevational view of the tab member of FIG. 37

FIG. 40 is a distal end view of the tab member of FIG. 37;

FIG. 41 is a perspective view of a seventh embodiment of the tab member;

FIG. 42 is a plan view of the tab member of FIG. 41;

FIG. 45 is a perspective view of an eighth embodiment of the tab member;

FIG. 46 is a plan view of the tab member of FIG. 45;

DESCRIPTION OF THE PREFERRED EMBODIMENTS

Figure 1:
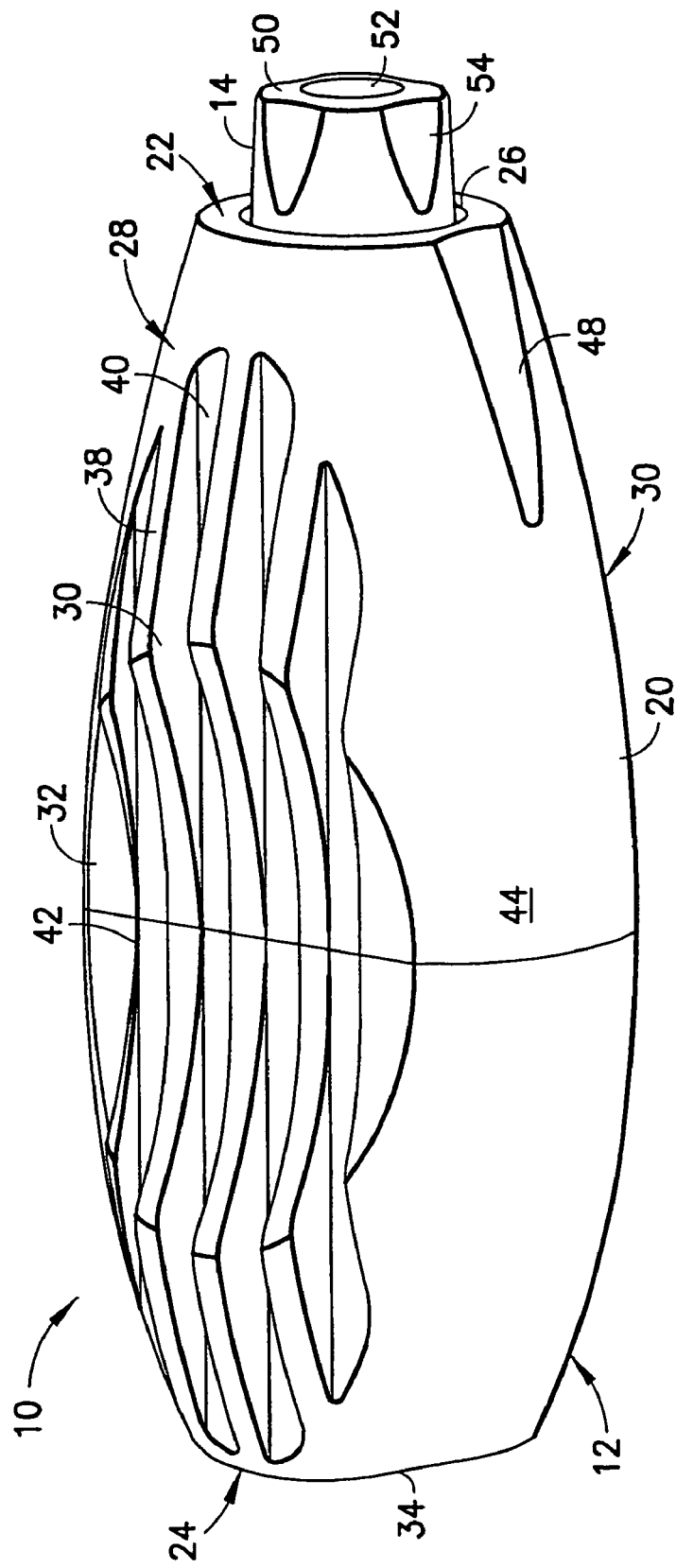
FIG. 1 is perspective view of a lancet device in accordance with an embodiment of the present invention.

For purposes of the description hereinafter, the words "upper", "lower", "right", "left", "vertical", "horizontal", "top", "bottom", "lateral", "longitudinal" and like terms, if used, shall relate to the invention, as it is oriented in the drawing figures. However, it is to be understood that the invention may assume many alternative variations and embodiments except where expressly specified to the contrary. It is also to be understood that the specific devices and embodiments illustrated in the accompanying drawings and described herein are simply exemplary embodiments of the invention.

Referring to FIGS. 1-7, a lancet device 10 according to the present invention is generally shown. The lancet device 10 generally includes a housing 12 and a shield 14 movably associated with the housing 12. As shown in FIGS. 7-48, discussed further herein, the lancet device 10 further includes a sterile tab member 16 adapted for association or connection with a puncturing element (not shown) disposed within the housing 12. The shield 14 is coaxially and movably associated with the housing 12. The shield 14 is further partially disposed within the housing 12 and extends outward from the housing 12.

Figure 51:
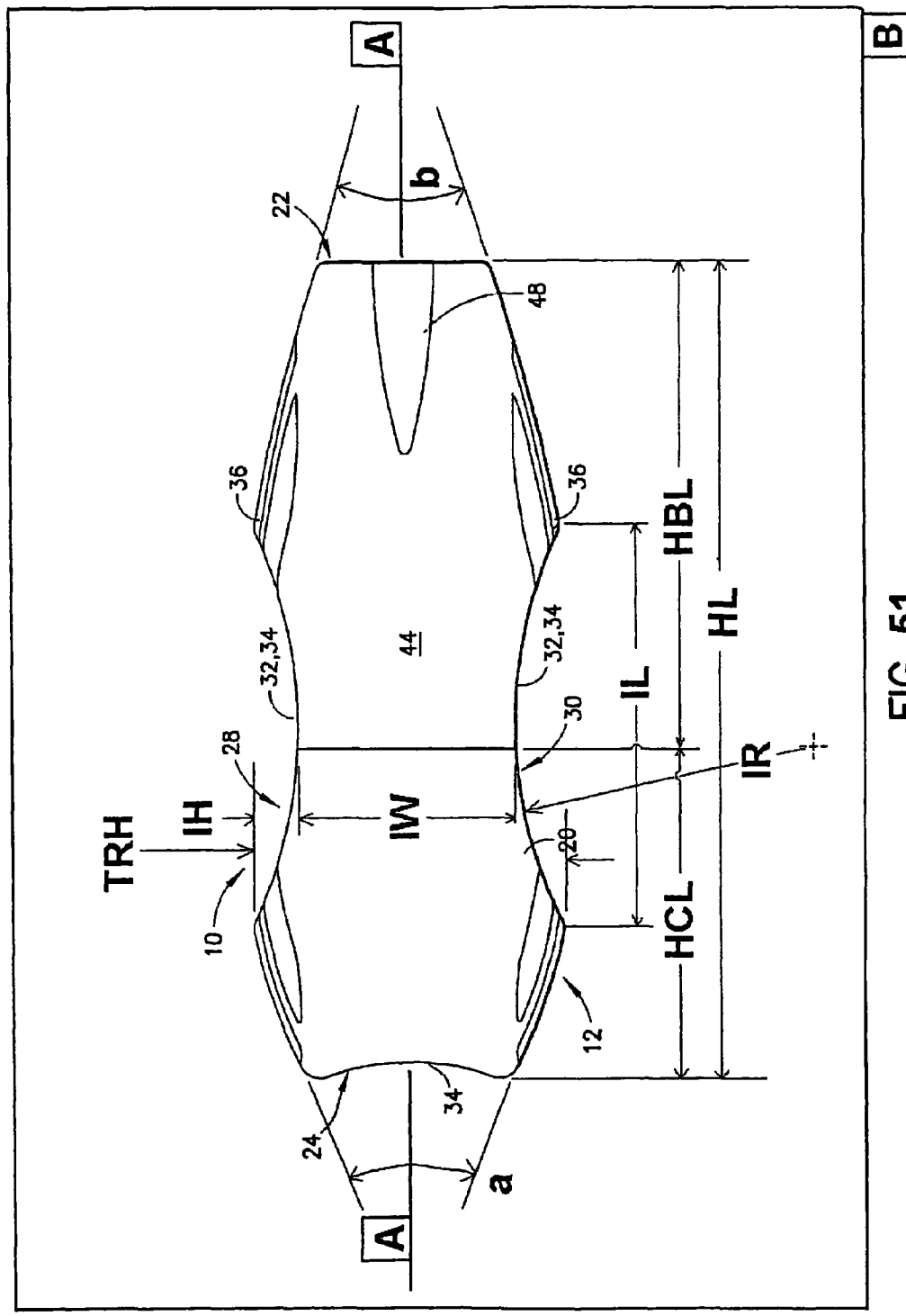
FIG. 51 is an opposite side elevational view of the lancet device of FIG. 1 with planes and dimensions shown.

The housing 12 has an elongated housing body 20 with a forward or distal end 22 and a rearward or proximal end 24. In one embodiment, the axial length of housing body 20 between the distal end 22 and proximal end 24, shown in FIG. 51 as housing length HL, is between 1.2 and 1.9 inches, such as between about 1.3 and about 1.7 inches, more typically between 1.4 and 1.6 inches. As shown in FIG. 1, the housing body 20 may comprise a distal portion and a separate proximal portion that mate near a mating line (adjacent element numbers "42" and "32" in FIG. 1). As shown in FIG. 51, housing base length HBL and housing cap length HCL represent the location of this mating line. The housing cap length, HCL, may be greater than 20% of HL in total length. For example, HCL may be between about 0.35 and 0.90 inches, such as between 0.50 and 0.74 inches, more typically between 0.60 and 0.68 inches. Alternately, the housing cap length HCL can be represented as a function of the length of the housing 12 as represented in FIG. 51 by HL. For example, the housing cap length may have a length HCL between about 0.23*HL and 0.59*HL, such as between 0.33*HL and 0.48*HL, and in particular between 0.39*HL and 0.44*HL in length.

Figure 52:
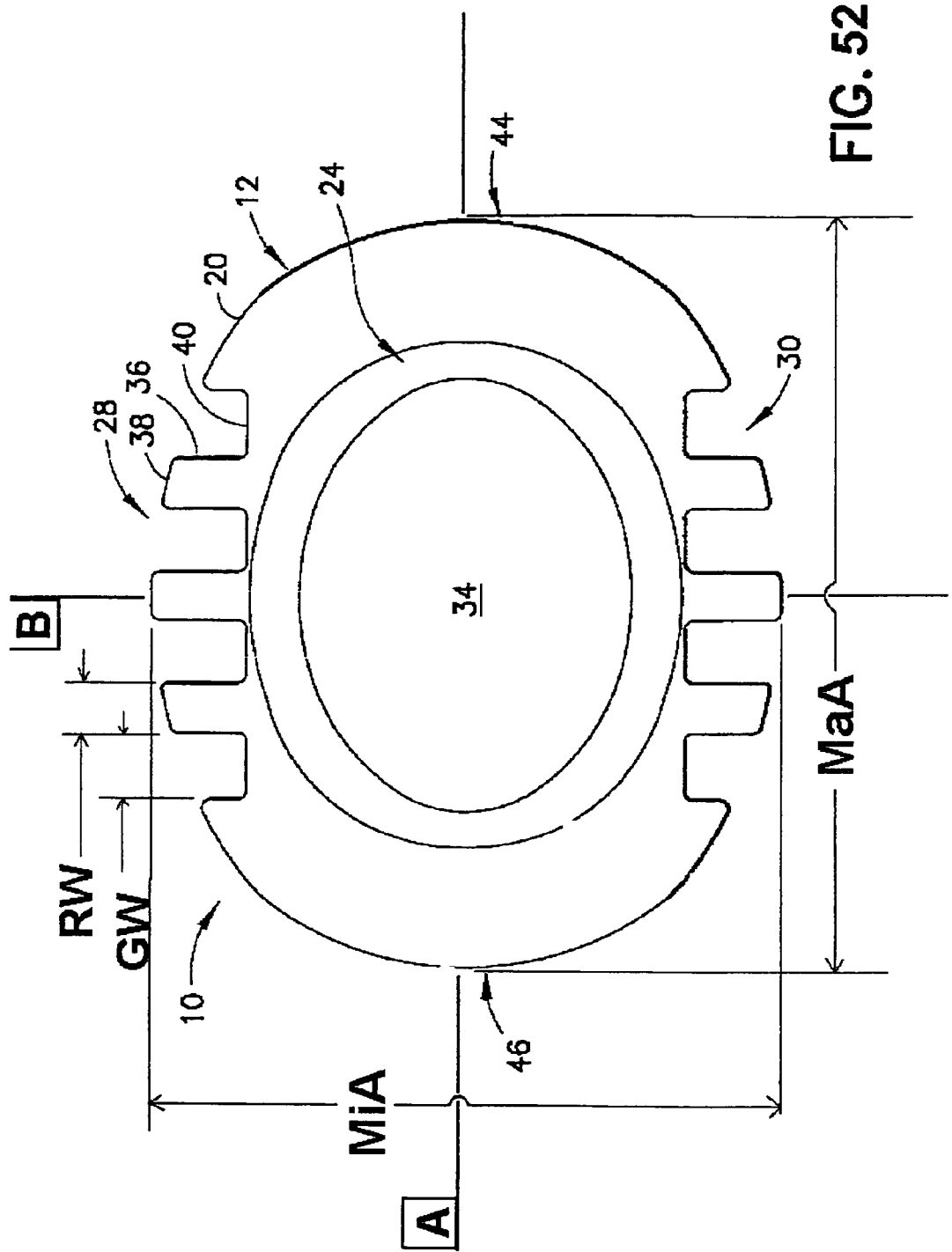
FIG. 52 is a proximal end view of the lancet device of FIG. 1 with planes and dimensions shown.

The forward or distal end 22 defines a forward or distal opening 26 through which the shield 14 extends and is coaxially associated with the housing body 20. The generally elongated housing body 20 has opposed lateral sides 28, 30 essentially symmetrically disposed about plane A as shown in FIGS. 51-52. The opposed lateral sides 28, 30 of the housing body 20 each define a finger grip such as indentation 32. While two opposed finger grip indentations 32 are provided on the housing body 20, it will be appreciated that only one finger grip indentation 32 formed in the housing body 20 may be provided in accordance with the present invention. The use of two opposed finger grip indentations 32 is preferred for ease of use and manipulation of the lancet device 10, as discussed further herein. The finger grip portions such as indentations 32 may be formed as concave depressions or recesses in the housing body 20, and may be formed from a plurality of longitudinally extending ribs 36, as will be described in more detail herein.

The rearward or proximal end 24 of the housing body 20 defines a rearward or proximal finger grip indentation 34. The proximal finger grip indentation 34 may also be formed as a concave depression or recess, but on the proximal end 24 of the housing body 20. The side finger grip indentations 32 and proximal finger grip indentation 34 provide ergonomically shaped surfaces that substantially conform to a user's fingertips to aid the user in manipulating the lancet device 10 and using the lancet device 10 in a blood letting, drawing, or collection procedure. The side finger grip indentations 32 and proximal finger grip indentation 34 provide multiple finger grip positions for the user. The multiple finger grip positions provided by the side finger grip indentations 32 and proximal finger grip indentation 34 improve the handling characteristics of the lancet device 10 by reducing the possibility of environmental factors, such as spilled blood, wetness, or other factors, from interfering with the positioning and actuation of the lancet device 10.

Figure 4:
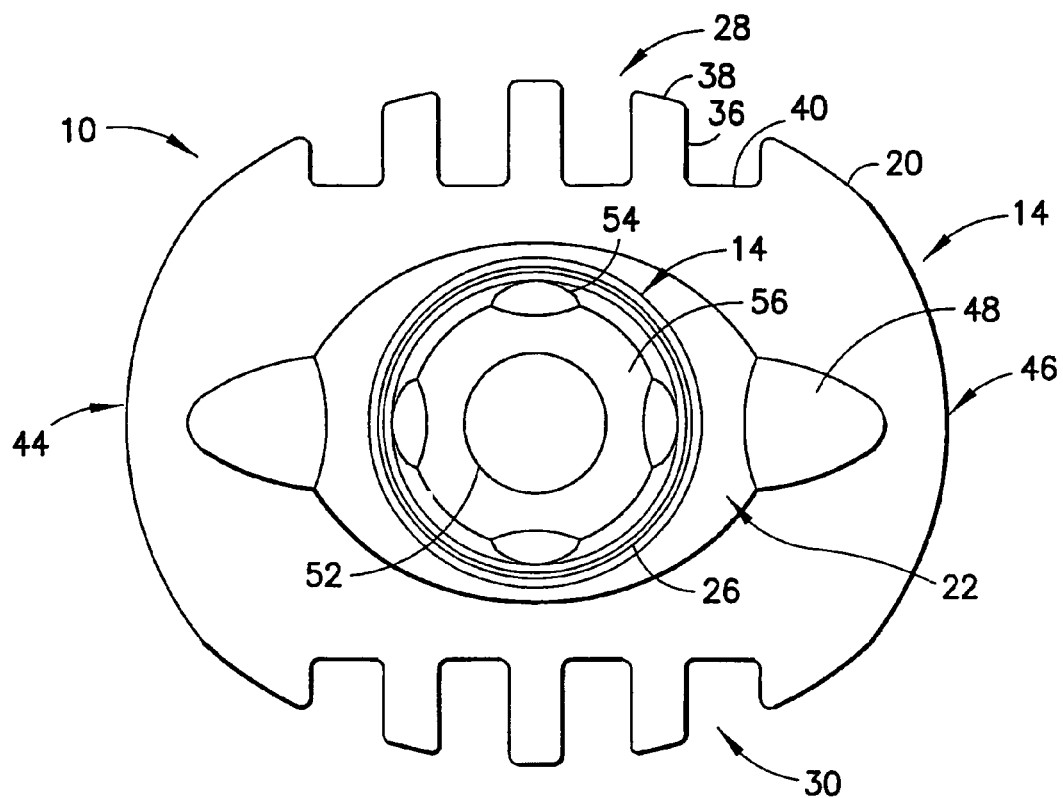
FIG. 4 is a distal end view of the lancet device of FIG. 1.
Figure 5:
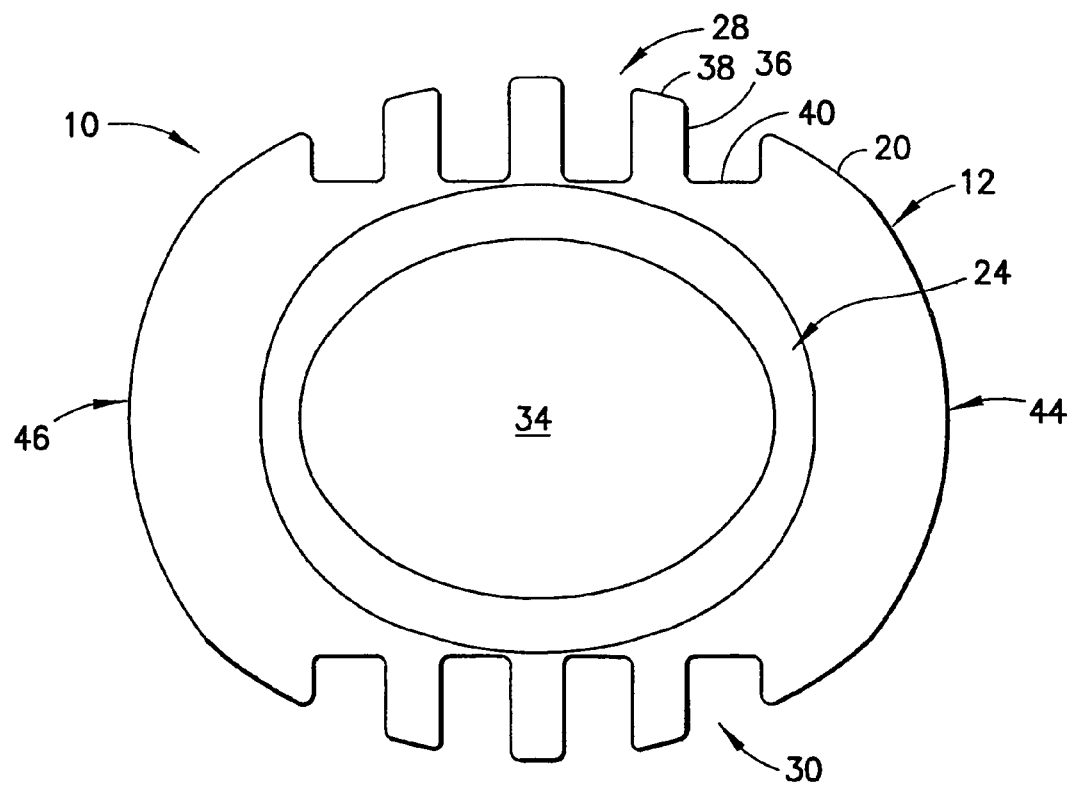
FIG. 5 is a proximal end view of the lancet device of FIG. 1.
Figure 6:
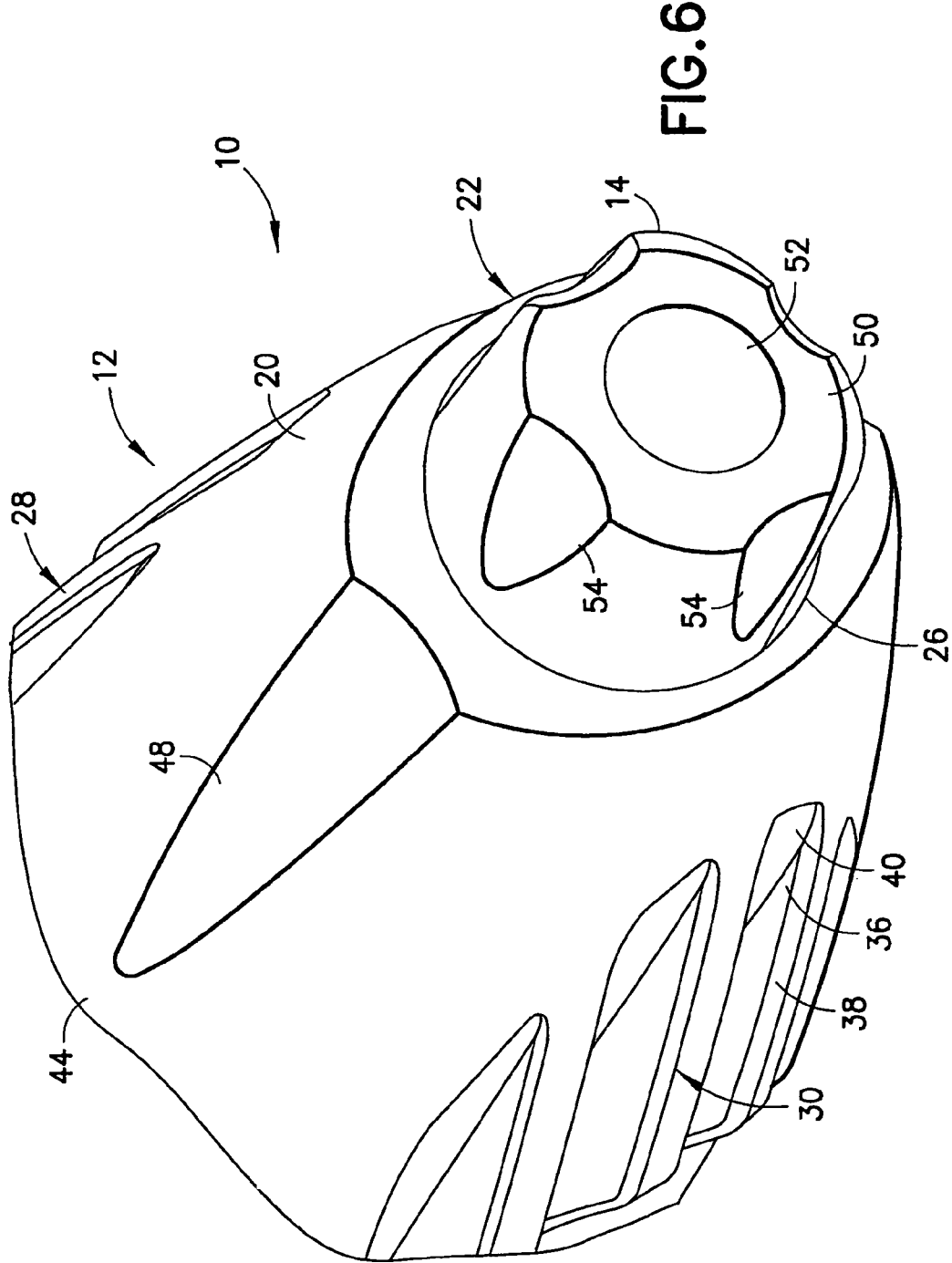
FIG. 6 is a perspective view of the distal end of the lancet device of FIG. 1.

The housing body 20 further includes a plurality of longitudinal ribs 36 extending along the housing body 20, and may be integrally formed with the housing body 20. The ribs 36 are disposed on the opposed sides 28, 30 of the housing body 20, essentially about plane A shown in FIGS. 51-52, and extend longitudinally along at least a portion of the length of housing body 20 approximately from the proximal end 24 to the distal end 22 of the housing body 20. The contour of ribs 36 generally defines the side finger grip indentations 32, with the ribs 36 extending through the depressed or recessed area defined by the finger grip indentations 32 in the housing body 20. The ribs 36 have generally rectangular cross-sections as shown in FIG. 4. However, tips 38 of the respective ribs 36 are contoured or tapered to generally match the generally oval cross-sectional shape of the housing body 20, and in particular the oval shape of the cross-section of housing body 20 formed adjacent the forward or distal end 22 and the rearward or proximal end 24. The ribs 36 define troughs 40 between each another. There is typically a total number of troughs 40 equal to the number of ribs 36 plus one. Therefore, as shown in FIG. 4, the number of troughs 40 is four while the number of ribs 36 is three. The ribs 36 generally improve the grip between the housing body 20 and the user's fingertips. The ribs 36, in combination with the side finger grip indentations 32, also provide a visual and tactile cue to the user to instruct the user where to place his or her fingertips. Furthermore, the ribs 36 each provide a means for reducing shrinkage voids that can happen after a molded component cools, especially for thick wall areas. As shown in FIG. 52, ribs 36 have a width RW and troughs 40 have a width GW. In one embodiment, the ribs 36 and troughs 40 have a width between about 0.02-0.09 inches, for example between about 0.03 and 0.07 inches, and in particular between 0.04 and 0.06 inches. The width of the ribs 36 and troughs 40 do not have to be equal to one another.

In general, the housing body 20 is symmetric about two planes A and B as shown in FIGS. 51 and 52, both substantially vertical and horizontal planes passing through the housing body 20 in the orientation of the housing body 20 shown in FIGS. 51-52. The symmetry of the housing body 20 is revealed about a substantially vertical plane A passing through the housing body 20. Plane B essentially passes through a longitudinal axis defined through either the centroid of the lancet device 10 or an axis defined by the puncture tip, tab member 16, or other features of the lancet device 10 that essentially have an axis. Plane B also is normal to (or perpendicular to) plane A and additionally passes through the axis.

As shown in FIG. 4, the housing body 20 has a generally oval-shape or prolate cross-section. The opposed sides 28, 30 of the housing body 20 form the long sides of the oval cross-section while the two remaining opposed sides 44, 46 form the two short sides of the oval cross-section and may be referred to as ends 44, 46. Moreover, the longitudinal cross-section of housing body 20 also has a generally oval-shape or prolate cross-section (as defined by the general cross-section of plane B shown in FIG. 52 and shown in FIG. 51). Such a general oval shape is defined, at least in part, by the contour of a portion of the longitudinal ribs 36 forming convex surfaces at opposed lateral sides 28, 30 adjacent the forward or distal end 22 and the rearward or proximal end 24, as shown in FIG. 51. Moreover, the finger grips are formed as indentations 32 on the opposed lateral sides 28, 30 of the housing body 20 in the form of concave shaped depressions or recesses in the outer surface of the housing body 20 for accommodating the fingertips of the user of the lancet device 10. Such finger grip indentations 32 are formed from a portion of longitudinal ribs 36 contoured to form a generally concave surface between the forward convex surface of ribs 36 adjacent the forward or distal end 22 and the rearward convex surface of ribs 36 adjacent the rearward or proximal end 24. The longitudinal ribs 36 forming the forward convex surface and the rearward convex surface are aligned through the concave surface defined by finger grip indentations 32, 34 along the length of housing body 20 at opposed sides 28, 30, and may continue as rib structures along the entire length of housing body 20, extending through the convex surface of ribs 36 defining finger grip indentations 32, 34.

The finger grip indentations 32 may be in the form of hyperbolic shaped indentations, recesses, or depressions in the opposed sides 28, 30 of the housing body 20 that define generally hyperbolic shapes in the opposed sides 30, 32 of the housing body 20. In addition or as an alternative to a hyperbolic shape, the fingergrip indentations may be parabolic or semicircular-shaped. As shown in FIG. 51, finger grip indentations 32 may have a radial curve defined by an indentation radius IR as shown in FIG. 51. In one embodiment, the radius IR is between about 0.5 and 1.2 inches, in particular between about 0.7 and 1.0 inches, and desirably between about 0.8 and 0.9 inches. This contour can be measured for instance by an optical comparator with radius measuring capability. Alternately, the radius IR can be represented as a function of the length of housing 12 as represented in FIG. 51 by HL. For instance, the radius IR may have a value between about 0.33*HL and 0.78*HL, such as between about 0.45*HL and 0.65*HL, in particular between about 0.52*HL and 0.59*HL.

As shown in FIG. 51, distal end 22 and proximal end 24 each taper based on the convex surfaces defined by the outer surfaces of ribs 36 at distal end 22 and proximal end 24, respectively. Such tapered sections based on the convex surfaces forms angles b and a at distal end 22 and proximal end 24 respectively. Each of the sides of angles b and a represent a tangent line extending from the end point of the convex surface defined by the outer surface of ribs 36 at distal end 22 and proximal end 24, respectively. The tapered sections are desirably symmetrical about plane A. In one embodiment, angle a, located adjacent proximal end 24, has an angle between about 25° and 55°, such as between about 29° and 45°, and more particularly between about 33° and 39°. Similarly, angle b, located adjacent distal end 22, has an angle which may be between about 18° and 39°, such as between about 22° and 32°, and more particularly between 24° and 28°.

Additionally, as shown in FIG. 51, the intersection of the convex surface defined by ribs 36 at the distal end 22 and proximal end 24 with the concave surface defined by ribs 36 which forms the finger grip indentations 32, 34 defines two corners that, when connected with a line (not shown), form a chord. This chord has a length IL at its centerline portion as represented in FIG. 51 which may be between about 0.3 and 1.3 inches, such as between about 0.5 and 1.0 inches, and more particularly between about 0.7 and 0.9 inches in length. Alternately, the chord length IL can be represented as a function of the length of housing 12 as represented in FIG. 51 by HL. For instance, the chord may have a length IL between about 0.2*HL and 0.85*HL, such as between 0.33*HL and 0.65*HL, and in particular between about 0.49*HL and 0.59*HL in length.

Furthermore, as shown in FIG. 51, the corners which form the ends of the chords (i.e. the intersection between the convex shape and the concave shape of ribs 36) are preferably symmetrically disposed about plane A. The distance between these corners forming the ends of the chords across the opposed lateral sides 32, 34 of housing body 20 is represented by TRH in FIG. 51. TRH may have a length between about 0.45 and 0.69 inches, such as between about 0.49 and 0.63 inches, and in particular between about 0.52 and 0.58 inches in length. Alternately, TRH can be represented as a function of the length of housing 12 as represented in FIG. 51 by HL. For instance, the TRH may have a length between about 0.29*HL and 0.45*HL, such as between about 0.32*HL and 0.41*HL, and more particularly between about 0.34*HL and 0.39*HL in length.

Furthermore, as shown in FIG. 51, the closest distance between finger grip indentations 32, 34 on housing 12 can be represented by dimension IW. IW must be smaller than dimension TRH and has the smaller of TRH or a length between about 0.29 and 0.49 inches, such as between about 0.33 and 0.45 inches, and desirably between about 0.36 and 0.42 inches in length. Alternately, IW can be represented as a function of the length of housing 12 as represented in FIG. 51 by HL. For instance, IW could have a length between about 0.19*HL and 0.32*HL, such as between about 0.22*HL and 0.29*HL, and more particularly between about 0.24*HL and 0.27*HL in length.

As shown in FIG. 52, housing body 20 essentially has a prolate contour, at least with respect to a cross-section through the housing body 20 at the corners which form the ends of the chords (i.e. the intersection between the convex shape and the concave shape of ribs 36). This outer body shape can also be described as elliptical or oval. In terms of ellipses, a minor axis (MiA) and major axis (MaA) represent the short and long chords respectively drawn through the center of foci. As shown in one embodiment in FIG. 52, the minor axis (MiA) and major axis (MaA) for the profile of housing body 20 may be about 0.56 and 0.70 inches respectively. The minor axis MiA may be between about 0.46 and 0.70 inches, more particularly between about 0.5 and 0.63 inches, for example between about 0.53 and 0.59 inches.

Additionally, the major axis MaA may be between about 0.53 and 0.85 inches, more particularly between about 0.6 and 0.8 inches, for example between about 0.65 and 0.75 inches. It should be noted that in the preferred embodiments, MaA is always larger than MiA.

Additionally, the ribs 36 each define a recessed portion or concave area 42 that defines the side finger grip indentations 32 in the housing body 20. The recessed portion 42 in each of the ribs 36 is formed in the tips 38 of the respective ribs 36 and, thus, the ribs 36 are not generally rectangular shaped in the recessed portions or areas 42. Further, the tips 38 of the ribs 36 are not tapered in this area. The recessed portion 42 in each of the ribs 36 generally matches or overlaps the depressed or recessed area defined by the side finger grip indentations 32, and this overlap area is both visually and tactilely communicated to the user of the lancet device 10 upon inspection and use. The user is intuitively instructed where to place his or her fingertips for operation of the lancet device 10. However, the primary function of the ribs 36 is to improve or enhance the grip between the user's fingertips and the housing body 20 for proper handling of the lancet device 10. Moreover, the recessed portion 42 formed by ribs 36 which generally defines the side finger grip indentations 32 is generally oval or elliptical in shape, as shown from the perspective view of FIG. 1.

Figure 2:
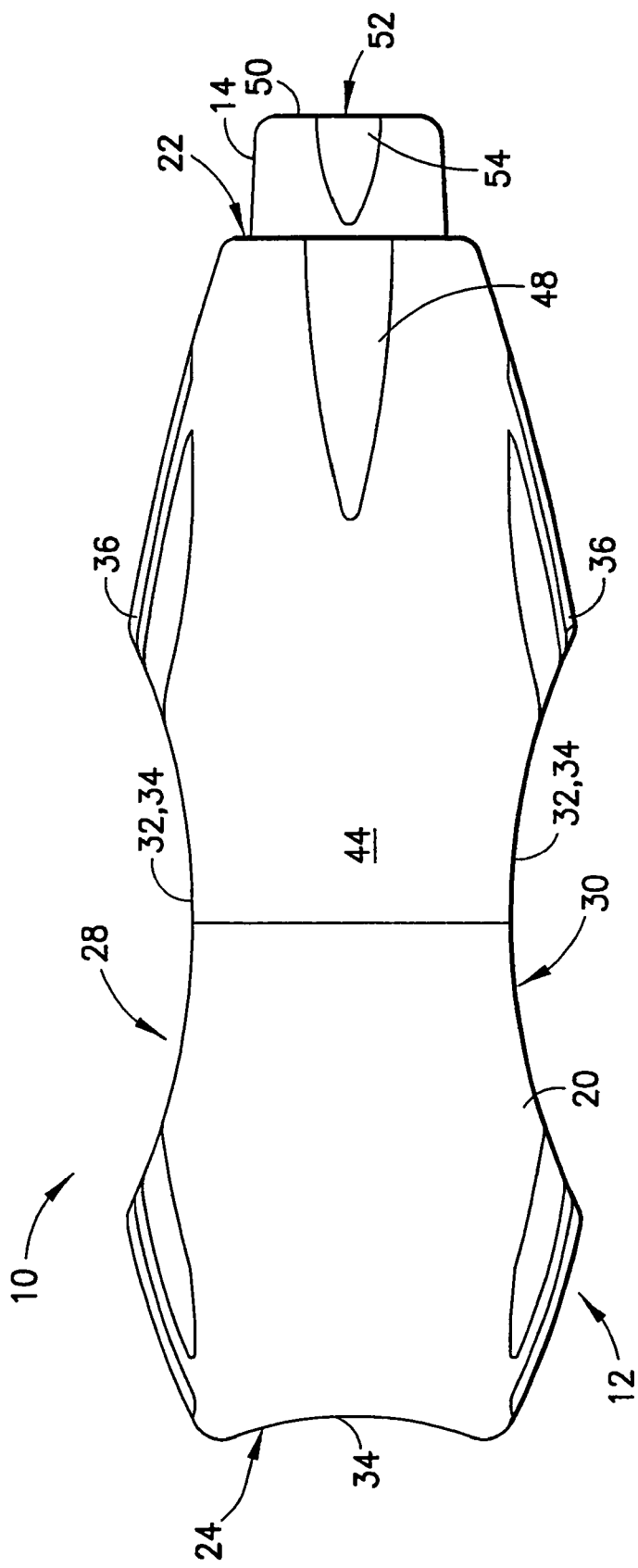
FIG. 2 is a side elevational view of the lancet device of FIG. 1.
Figure 3:
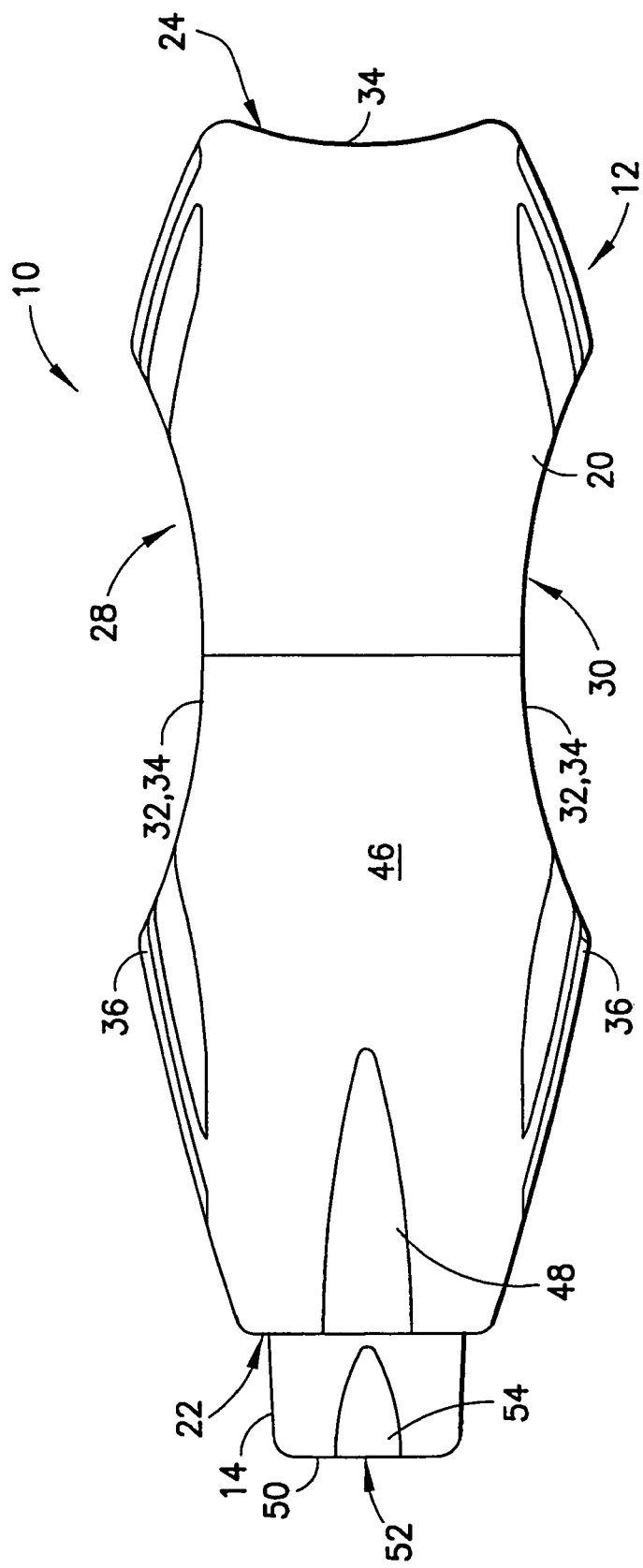
FIG. 3 is an opposite side elevational view of the lancet device of FIG. 1.

The housing body 20 further defines at least one and optionally two or more peripheral indentations 48. As shown in FIGS. 2 and 3, the peripheral indentations 48 are defined in the opposed ends 44, 46 of the housing body 20. The peripheral indentations 48 are generally U-shaped and are formed as substantially concave depressions or recesses in the housing body 20.

The shield 14 extends outward from the distal opening 26 in the housing body 20, as indicated previously. The shield 14 is a generally cylindrical structure having a distal end wall 50 defining a centrally located distal opening 52 through which the puncturing element extends when the lancet device 10 is actuated by the user. The distal end wall 50 generally defines a small contact area about the distal opening 52 for contacting the intended area on the user's body which is to be punctured by the puncturing element. The reduced contact area is made smaller (i.e., reduced in area) by a plurality of peripheral indentations 54 that are formed in the shield 14. The peripheral indentations 54 visually aid the user in aiming the lancet device 10 generally, and aiming the puncturing element in particular. The peripheral indentations 54 generally resemble the peripheral indentations 48 provided on the housing body 20, and are generally U-shaped concave depressions or recesses. The peripheral indentations 54 are positioned around the perimeter of the shield 14 and may be equally spaced about the shield 14. The peripheral indentations 54 enable the user to easily visually locate the approximate discharge point of the puncturing element, thereby improving the aiming characteristics of the lance device 10 and ensuring optimal blood flow during a skin puncturing operation. One or more of the peripheral indentations 54 may be radially aligned with one or more peripheral indentation 48. The peripheral indentations 48, 54 may define indented shapes or contours that act as focus "targets" for indicating to the user where the approximate discharge point of the puncturing element is likely to be from the shield 14. The indented shapes or contours may be parabolic, elliptical, semicircular, etc., and be positioned on the housing body 20 and shield 14 to focus or direct the user to properly target the lancet device 10. For example, one or more of the peripheral indentations 54 may be radially aligned with one or more peripheral indentations 48 to facilitate aiming of the lancet device 10 at a chosen puncture position on the body of patient.

Figure 7:
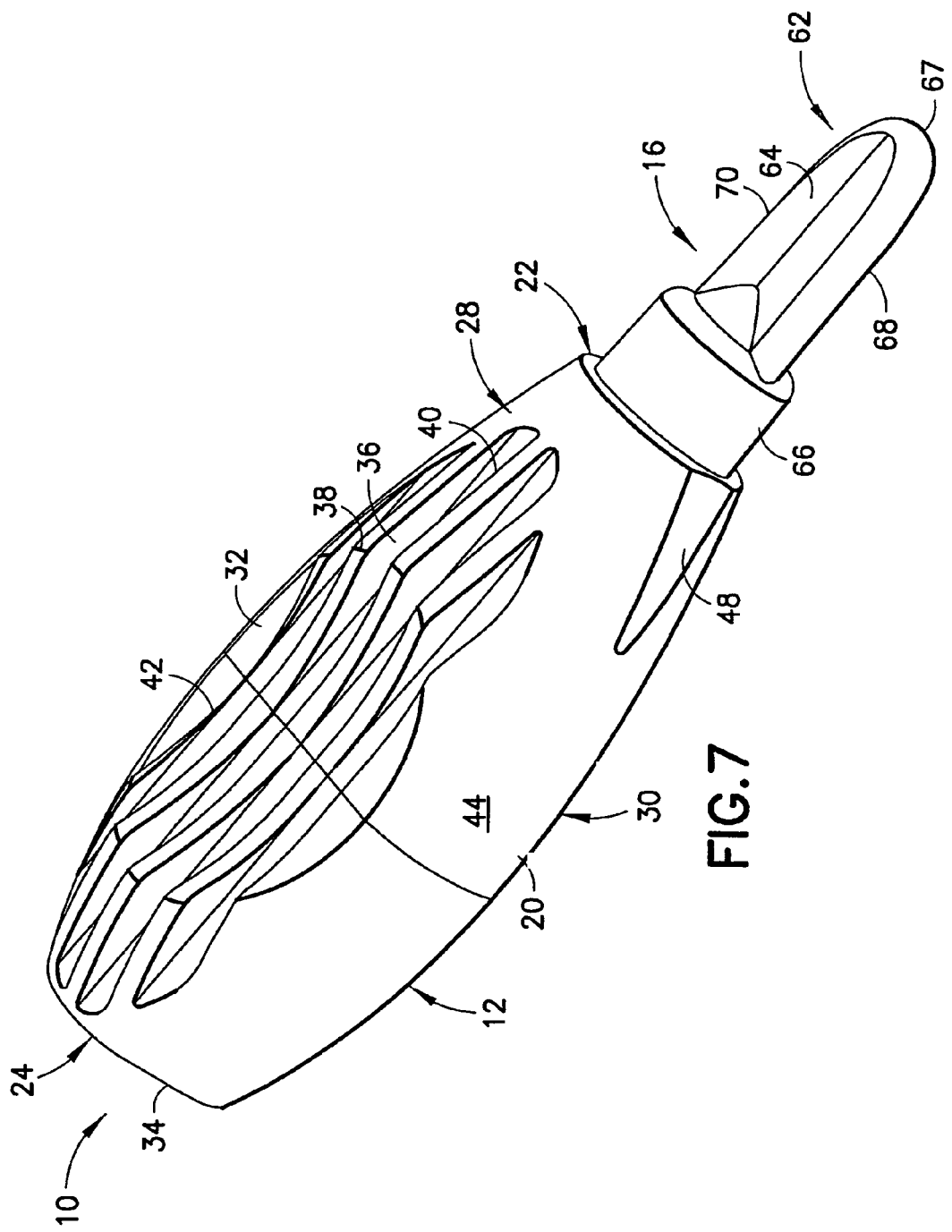
FIG. 7 is a perspective view of the lancet device shown with a removable sterile tab member according to a first embodiment.
Figure 7A:
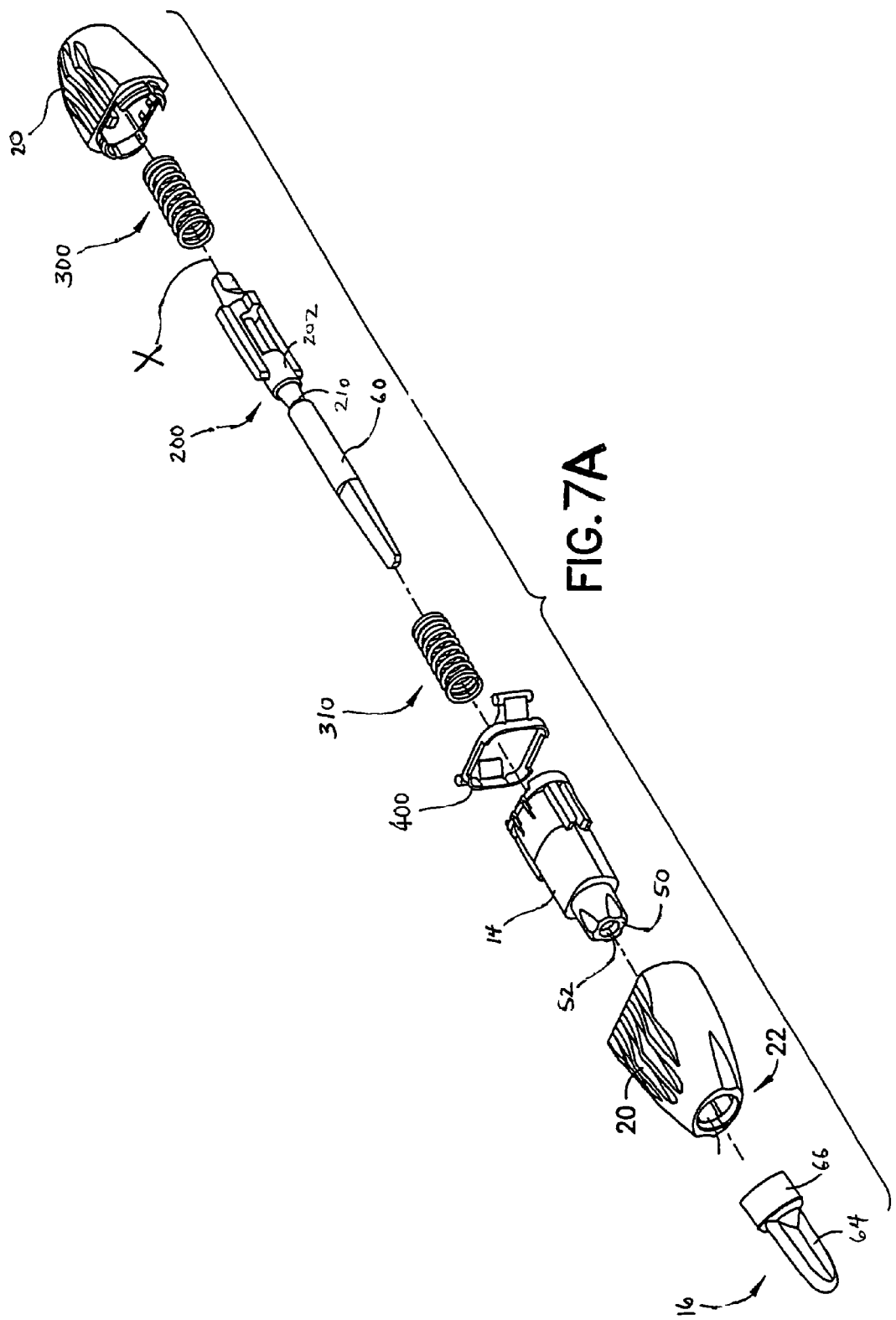
FIG. 7A is an exploded perspective view of a lancet device showing the internal actuation mechanism in accordance with an embodiment of the invention.

The housing 12 is generally used to enclose an actuating mechanism, shown in one particular arrangement in FIG. 7A. The actuating mechanism is used to retain the puncturing element prior to conducting a skin puncturing procedure and release the puncturing element upon actuation of the actuating mechanism by the user. The actuating mechanism utilizes the relative movement between the shield 14 and the housing 12 when the shield 14 is displaced into the housing 12 as the input movement or force to release the puncturing element for the skin puncturing procedure. Generally, in operation, the lancet device 10 is actuated by the user gripping the device 10 between a thumb and finger on each of the respective finger grip indentations 32, 34, and placing the forward end 50 of the shield 14 against the location on the user's body or another person's body where it is desired to initiate blood flow. Once placed against the body, the user applies axial pressure at the finger grip indentations 32, 34 toward the forward or distal end 22 of the housing body 20, exerting a distally directed force on the housing body 20 which causes the shield 14 to move from a first position (with the forward end 50 extending out of the forward end 22 of the housing 12) to a second position into the housing 12. As indicated, the movement of the shield 14 into the housing 12 may be used as the input to actuate the actuating mechanism and cause release of the puncturing element. Suitable actuating mechanisms for this purpose are disclosed in U.S. Provisional Patent Application Ser. Nos. 60/569,479 filed May 7, 2004, entitled "Rotary-Actuated Medical Puncturing Device", or 60/572,317 filed May 19, 2004, and entitled "Cam-Actuated Medical Puncturing Device", the disclosures of which are incorporated herein in their entirety by reference thereto.

Another suitable actuating mechanism is disclosed in co-pending U.S. Provisional Patent Application Ser. No. 60/631,846 filed Nov. 30, 2004, and co-pending U.S. application Ser. No. 11/123,849 filed May 6, 2005 entitled "Contact Activated Lancet Device", the disclosures of which are incorporated herein in their entirety by reference thereto. Such an actuating mechanism is substantially shown in FIG. 7A herein. In particular, the housing 20 generally includes a forward body portion and a rearward body portion, which are matable to define housing 12. Shield 14 is disposed within housing body 20 and extends through the distal end 22 thereof. A lancet assembly 200 is further provided for axial movement through housing body 20 and shield 14 along axis X. Lancet assembly 200 includes a lancet structure 202 including a lance tip (not seen) at a forward end thereof, with post 60 covering or encompassing the lance tip. Post 60 is attached to lancet structure 202 at a separable notch portion 210, such that separation of post 60 from lancet structure 202 at notch portion 210 exposes the lance tip for use. Lancet assembly 200 is movable through housing body 20 and shield 14 based on a biasing force of spring 300, and is retractable back within housing body 20 and shield 14 based on a retraction force of spring 310. An actuator 400 maintains lancet assembly 200 in a pre-activated state within housing body 20. When shield 14 is caused to move within housing body 20, shield 14 effects movement of actuator 400, which then operates to release lancet assembly 200 from a maintained state, permitting the spring 300 to bias the lancet assembly 200 to a puncturing position and permitting retraction spring 310 to retract the lancet assembly 200 back within the housing body 20 and shield 14. Such operation is more fully described in U.S. Provisional Patent Application Ser. No. 60/631,846 and U.S. application Ser. No. 11/123,849 noted above.

Referring further to FIGS. 7-16, a sterile tab member 16 according to one embodiment is illustrated in connection with the lancet device 10. In the first embodiment of the tab member 16, the tab member is associated with the distal end 22 of the housing body 20 and encompasses or encloses the shield 14. In each of the embodiments of the tab member 16 to be discussed in this disclosure, the primary function of the tab member 16 is to enclose and shield the puncturing element, i.e. the lance tip, contained within the housing body 20 prior to actuating the lancet device 10. To use the lancet device, the tab member 16 must first be removed from the puncturing element. The tab member 16 is generally associated with the lancet assembly and may be integrally molded to a portion of the lancet assembly during a molding process. For example, during such a molding process, the tab member 16 may be integrally molded with the lancet structure of the lancet assembly and molded to enclose the puncturing element or lance tip. To use the lancet device 10, the tab member 16 must be separated from the lancet structure by breaking the integral connection between the tab member 16 and the lancet structure such as through a separable notch and then be removed from the lancet structure to expose the lance tip. The applied breaking force is in accordance with the present invention and may be a singular twisting or pulling motion, or a combined "twisting" (i.e., rotational) and "pulling" motion applied to the tab member 16.

An alternative connection between the tab member 16, lancet structure, and puncturing element, the tab member 16 may be secured only to the puncturing element by methods customary in the medical field, such as with a medical grade adhesive. In this alternative connection, a suitable "twisting" and "pulling" breaking force must be applied to the tab member 16 to remove the tab member 16 from the puncturing element.

The tab member 16 shown in FIGS. 7-16 is a two-piece structure formed by an inner portion including a post portion 60 and an outer portion defining distal portion 62. The post portion 60 is generally adapted to enclose the puncturing element and maintain the sterility of the puncturing element until the lancet device 10 is to be used. The distal portion 62 is formed to enclose the distal opening 52 in the forward distal end 50 of the shield 14, and is adapted to maintain the shield 14 and the housing 12 from axially moving with respect to each other. The distal portion 62 is also formed ergonomically to allow the user to easily manipulate the tab member 16 and apply the necessary breaking force to release the tab member 16 from engagement with the actuating mechanism and/or puncturing element contained in the housing body 20. The distal portion 62 includes a grip portion such as paddle-shaped member 64 adapted to be grasped by the user for applying the necessary breaking force. In the present embodiment of the tab member 16, the distal portion 62 includes a depending skirt 66 that is adapted to cooperate with (i.e., generally encompass or enclose) the shield 14. The paddle-shaped member 64 has a rounded distal end 67.

Figure 12:
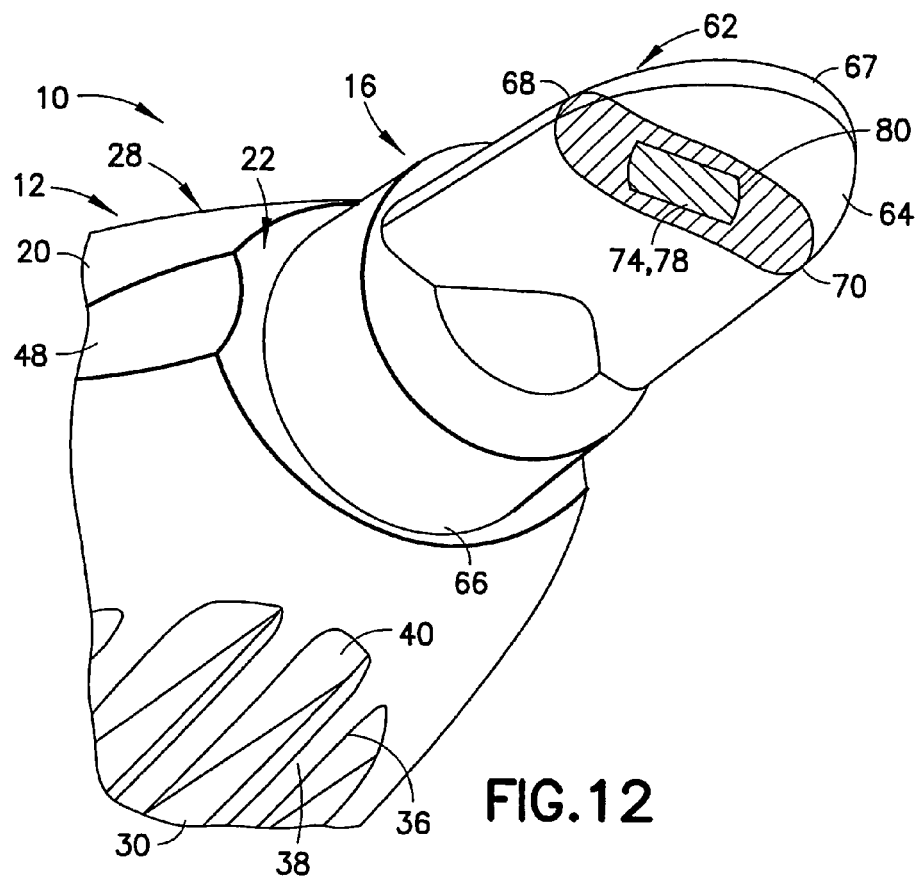
FIG. 12 is perspective and partial cross-sectional view of the lancet device of FIG. 7 showing a cross-section of the tab member.
Figure 13:
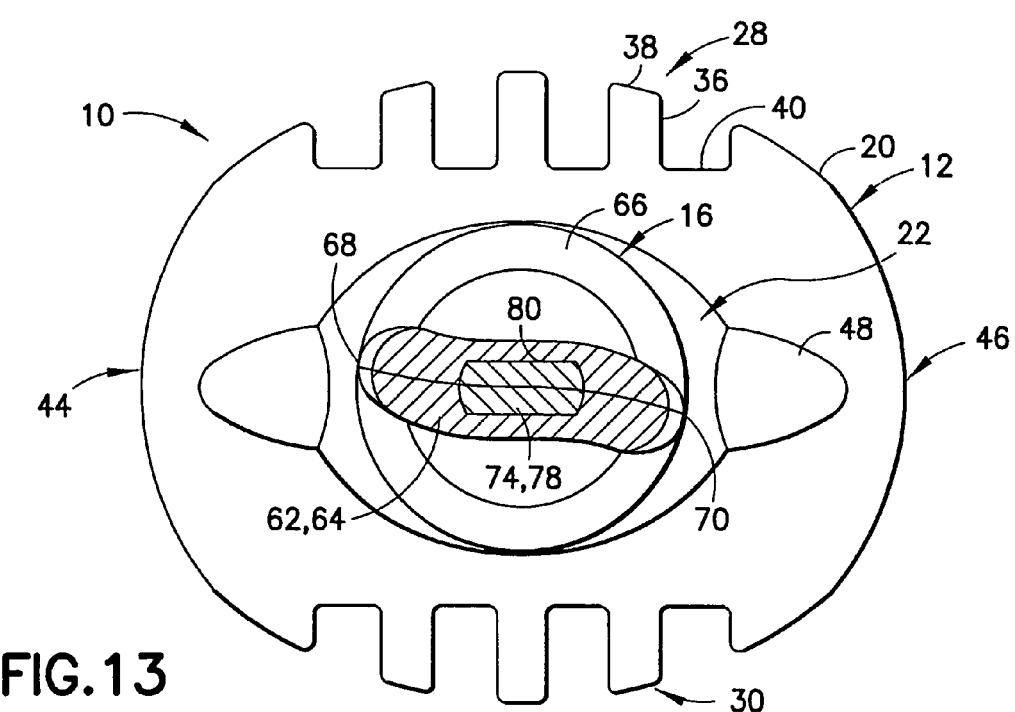
FIG. 13 is a distal end view and partial cross-sectional view of the lancet device of FIG. 7 showing a cross-section of the tab member.

The opposed sides of the paddle-shaped member 64 exhibit contouring to guide the user as to where to place his or her fingertips on the paddle-shaped member 64, and to visually and tactilely indicate to the user how to apply the breaking force to the tab member 16 to break the connection between the tab member 16 and actuating mechanism and/or the puncturing element. The contouring is formed by oppositely curved opposed edges 68, 70 of the paddle-shaped member 64. The oppositely curved opposed edges 68, 70 form a generally non-symmetrical cross-section about a plane passing substantially transversely through the paddle-shaped member 64 (i.e., generally perpendicular to the plane revealing the cross section depicted in FIG. 13, for example). The cross-section shown in FIGS. 12 and 13 is generally wave or S-shaped. In summary, in addition to providing a visual and tactile cue as to where the user should place his or her fingertips on the paddle-shaped member 64, the contouring of the paddle-shaped member 64 also indicates both visually and tactilely to the user that rotational force should be applied to the paddle-shaped member 64 to aid in separating the tab member 16 from the actuating mechanism and/or puncturing element disposed within the housing body 20. The breaking force is intended to be a combined rotational or "twisting" force and "pulling" force for breaking the connection between the tab member 16 and the actuating mechanism and/or puncturing element.

Figure 8:
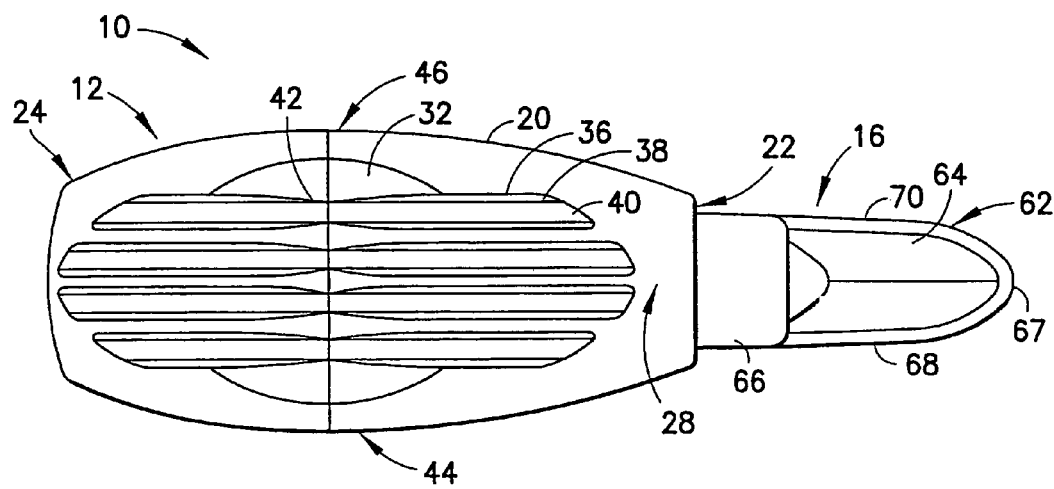
FIG. 8 is a plan view of the lancet device of FIG. 7.
Figure 9:
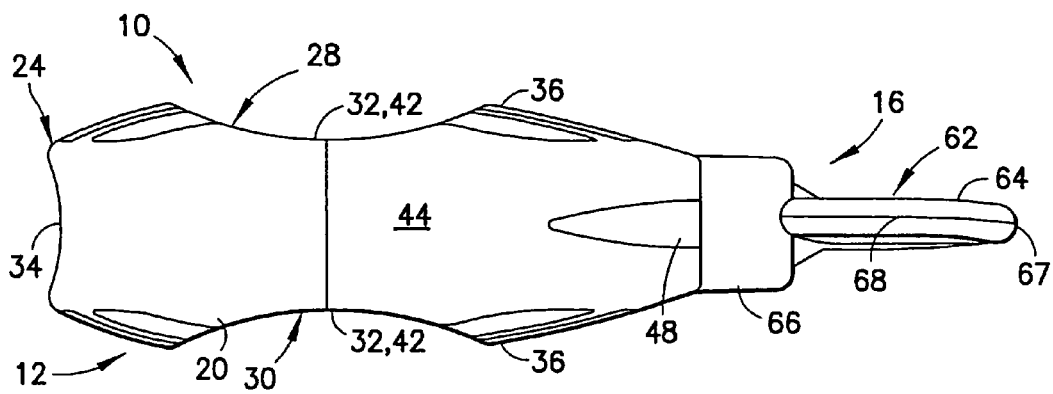
FIG. 9 is a side elevational view of the lancet device of FIG. 7.
Figure 10:
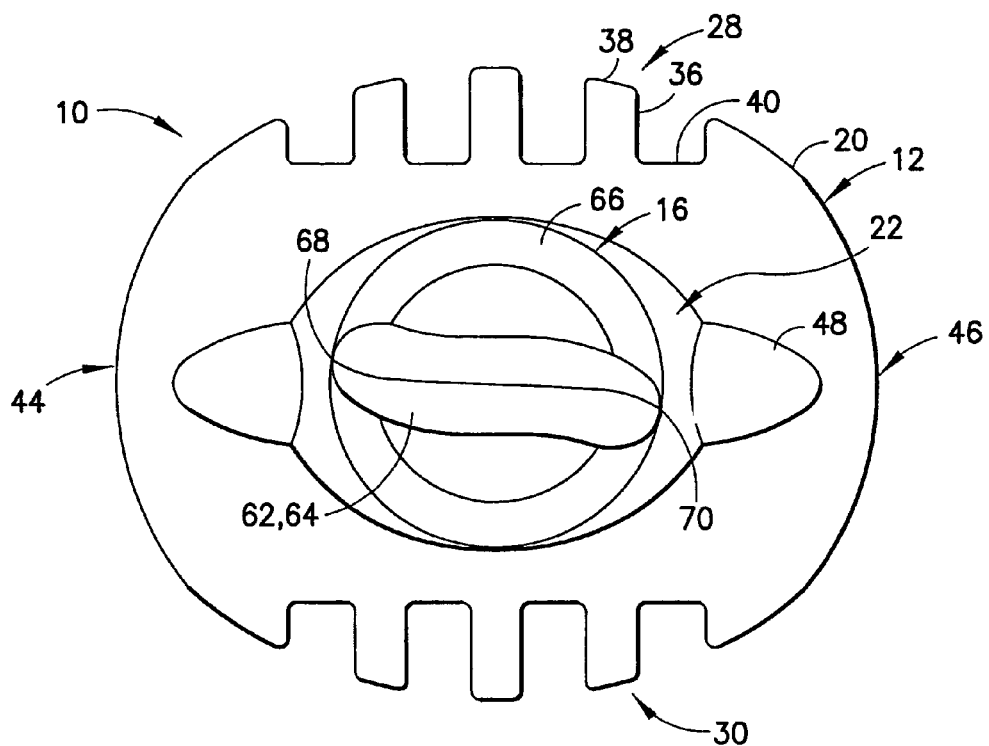
FIG. 10 is a distal end view of the lancet device of FIG. 7.
Figure 11:
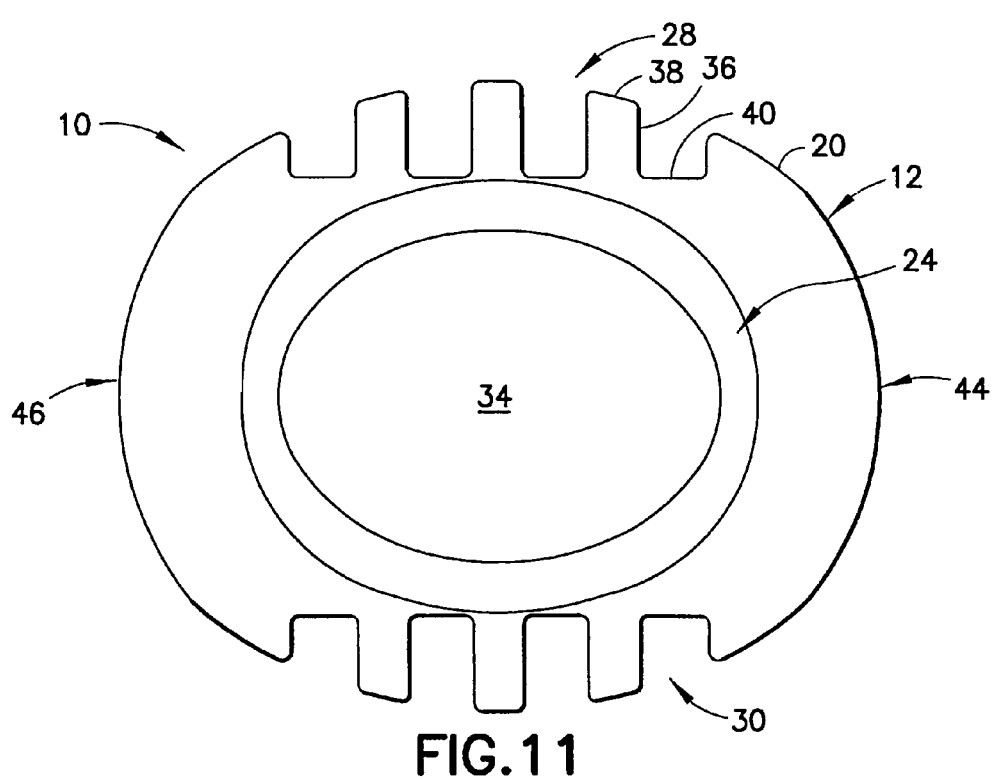
FIG. 11 is a proximal end view of the lancet device of FIG. 7.
Figure 14:
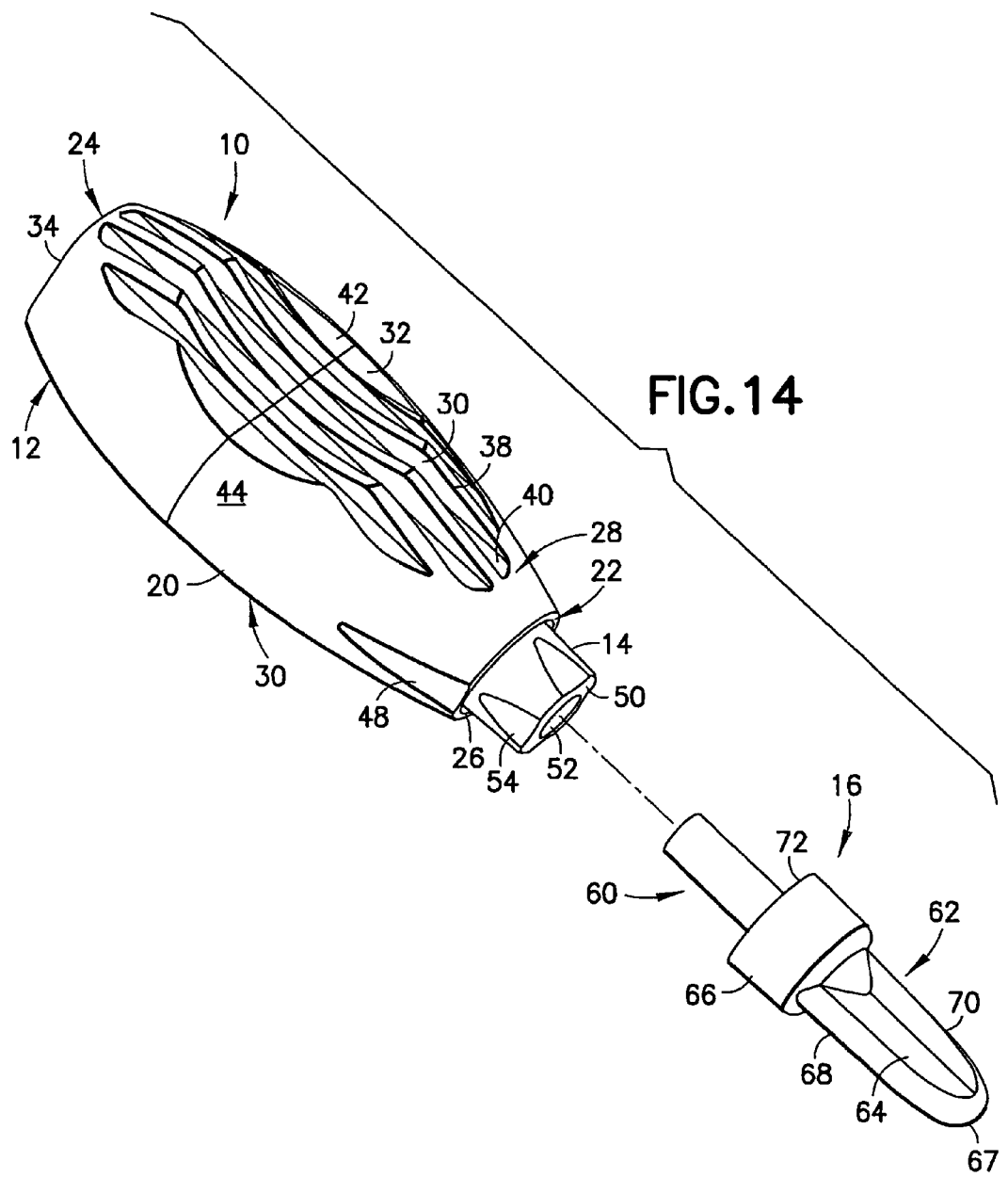
FIG. 14 is an exploded perspective view of the lancet device of FIG. 7 showing the tab member separated from the body of the lancet device.
Figures 15, 16:
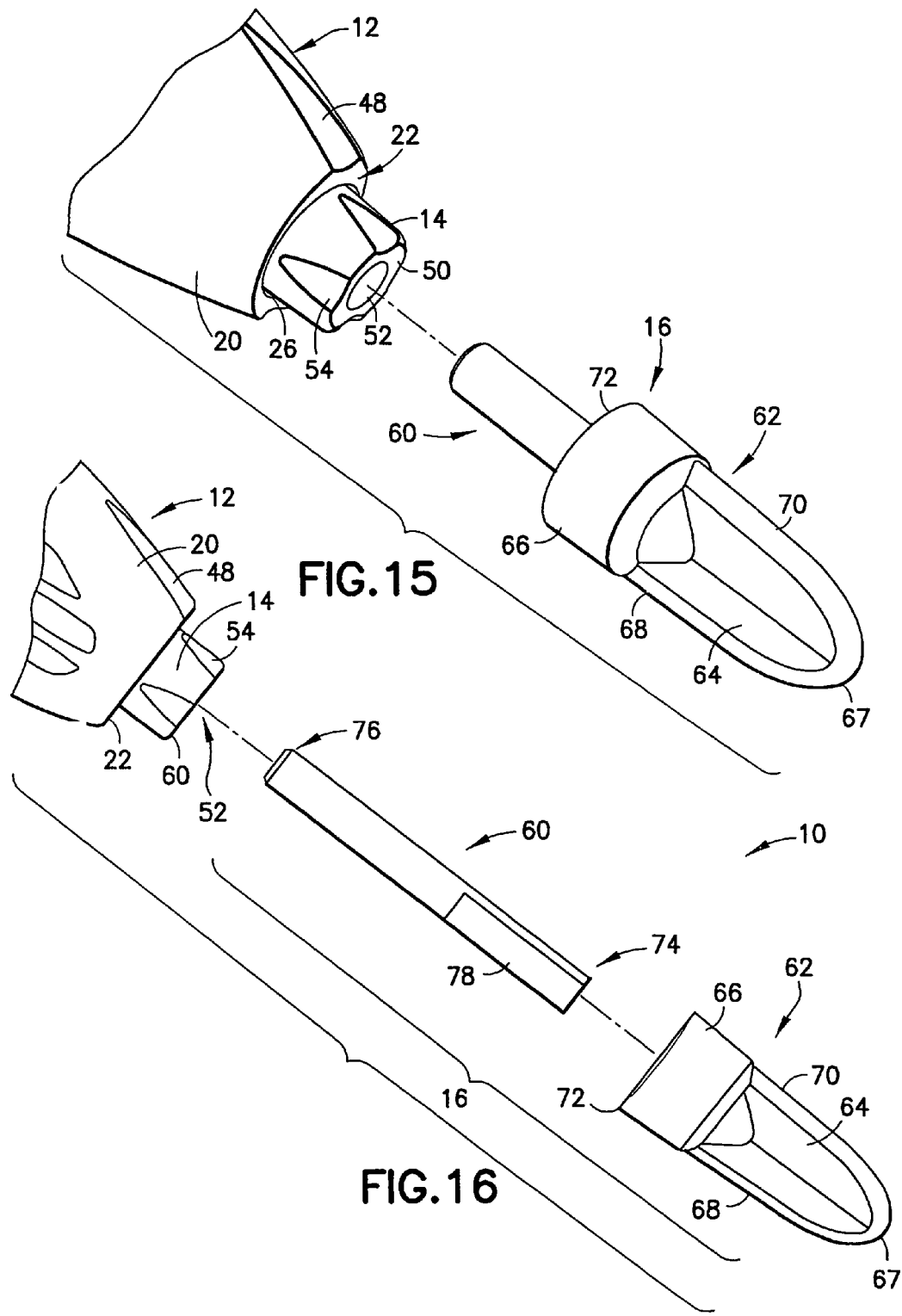
FIG. 15 is a close-up and rotated perspective view of the lancet device and tab member of FIG. 14.
FIG. 16 is an exploded perspective view of the lancet device and tab member of FIG. 15, showing separable components of the tab member.
Figure 17:
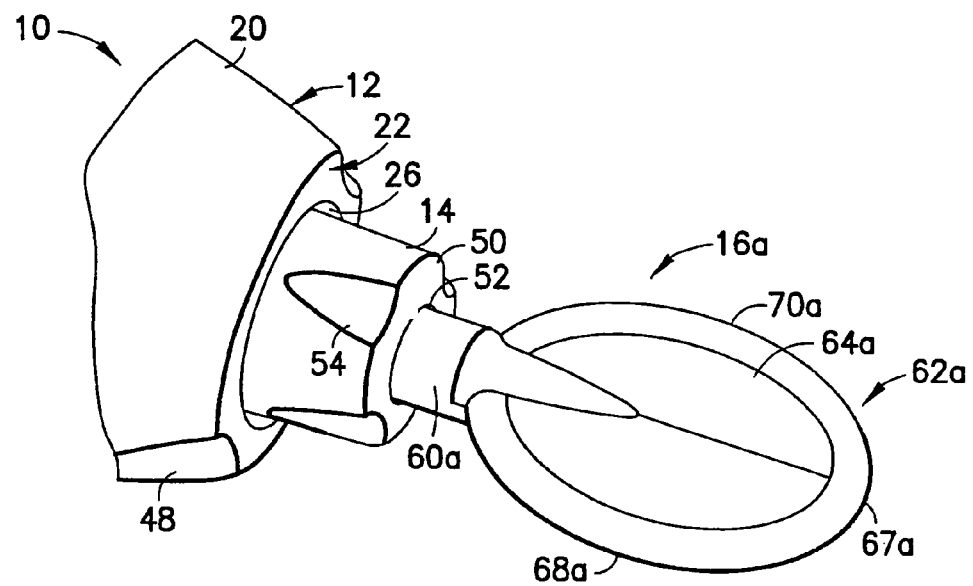
FIG. 17 is a perspective view of the distal end of the lancet device with a second embodiment of the tab member.
Figure 18:
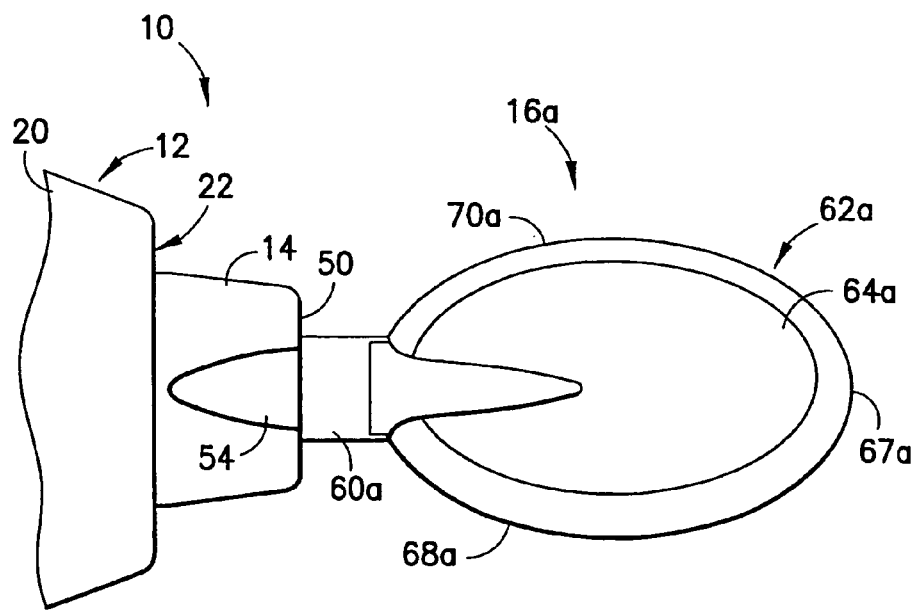
FIG. 18 is a plan view of the lancet device of FIG. 17.
Figure 19:
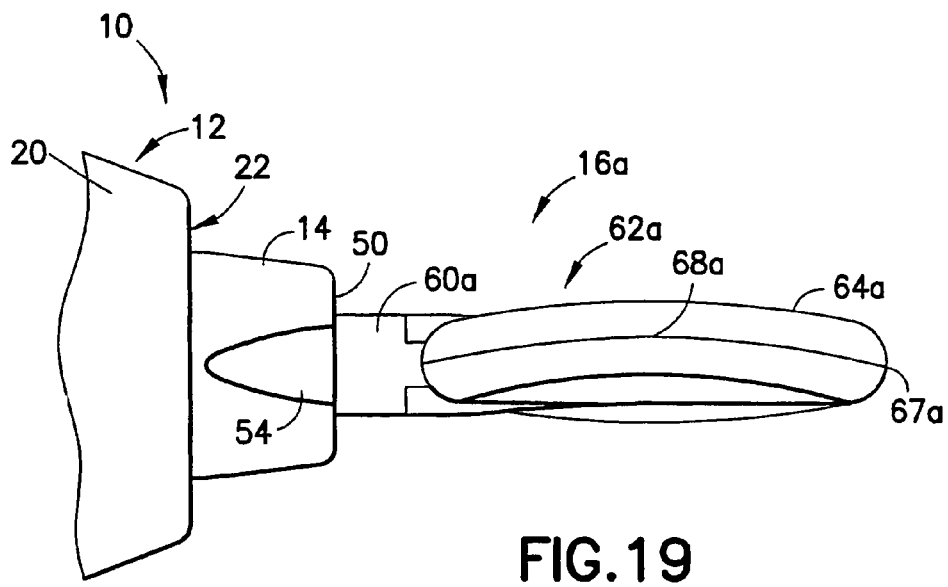
FIG. 19 is a side elevational view of the lancet device of FIG. 17.

As shown in FIGS. 7-9 in particular, the skirt 66 generally encompasses or encloses a distal portion of the shield 14 in the pre-use state of the lancet device 10. This aids in maintaining sterility of not only the puncturing element within the device, but also sterility of the forward face of distal end 50 of shield 14 which contacts the patient's skin during use. The skirt 66 also acts to prevent unintended actuation of the lancet device 10. As shown in FIGS. 14-16, the skirt 66 is an integral part of the distal portion 62 and is continuous with the paddle-shaped member 64. The skirt 66 includes a circumferential edge 72 that engages the distal end 22 of the housing body 20 when the tab member 16 is associated with the shield 14, which prevents the shield 14 from being inadvertently displaced into the housing 12 and thereby causing inadvertent actuation of the lancet device 10. The housing 12, shield 14, and tab member 16 are all preferably formed of molded plastic material, such as a medical grade plastic material. The skirt 66 may also be provided as part of any of the additional embodiments of the tab member 16 to be discussed herein.

In an alternate embodiment, the skirt 66 and/or the housing body 20 may include structure to facilitate removal of the tab member from the lancet device 10. For example, as shown in FIG. 14A the circumferential edge 72 of the skirt 66 and the distal end 22 of the housing body 20 may include corresponding structure to facilitate removal of the tab member 16 from the device 10. In the embodiment of FIG. 14A, circumferential edge 72 and distal end 22 are both contoured with a corresponding profile. When skirt 66 is engaged with shield 14 prior to use, the corresponding profile of circumferential edge 72 and distal end 22 mate to form an enclosed structure. During removal, rotation of tab member 16 causes the circumferential edge 72 of skirt 66 to ride along the contoured surface of distal end 22, thereby creating or effecting a cam-like engagement between the respective contoured surfaces, and facilitating forward or distal movement of tab member 16, assisting in the removal of tab member 16.

In operation, the paddle-shaped member 64 interferes with activation or movement of the shield 14 and, therefore, activation of the lancet device 10 generally. The circumferential edge or surface 72 is positioned to engage, for example, by contacting, the distal end 22 of the housing body 20, whereby the shield 14 cannot be displaced into the housing body 20 to impart the motion or force necessary to activate the actuating mechanism disposed within the housing body 20. Accordingly, the paddle-shaped member 64 is an activation inhibiting or interfering device preventing movement of the shield 14 into the housing body 20 and, therefore, the lancet device 10 generally.

With reference, in particular, to FIG. 16, the tab member 16 is a two-part structure formed by the post portion 60 and distal portion 62, as was indicated previously. The post portion 60 may be separated from the distal portion 62, as illustrated in FIG. 16. The post portion 60 includes a distal end 74 and a proximal end 76. The proximal end 76 is generally adapted for connection to the actuating mechanism and/or puncturing element disposed in the housing 12, for example an integral connection with a portion of the actuating mechanism. The distal end 74 defines a tapered portion 78 to allow the distal end 74 to be inserted into a receiving recess 80 in the distal portion 62 and, more particularly, in the paddle-shaped member 64. The engagement between the distal end 74 and the receiving recess 80 is a friction fit engagement, and the distal end 74 may be removed from the receiving recess 80, thereby separating the post portion 60 and distal portion 62. In all embodiments of the tapered portion 78, the cross section of 78 taken perpendicular to a central axis through the distal end 74 produces a non-circular section, such that rotation of the post portion 60 with respect to the distal portion 62 and paddle-shaped member 64 is prevented or at least resisted.

Referring to FIGS. 17-22, the lancet device 10 is shown with a second embodiment of the tab member 16a. The tab member 16a is generally similar in configuration to the tab member 16 discussed previously with two minor changes. First, the tab member 16a omits the skirt 66 from the distal portion 62a. Additionally, the overall shape of the paddle-shaped portion 64a is generally oval-shaped or prolate. The second embodiment of the tab member 16a illustrates that the skirt 66 is optional and the shield 14 may be left exposed in accordance with the present invention. However, as indicated previously, the skirt 66 may be used with any of the embodiments of the tab member 16 embodiments set forth in this disclosure, or be omitted from any of the embodiments as indicated by the disclosure of FIGS. 17-22.

Figure 20:
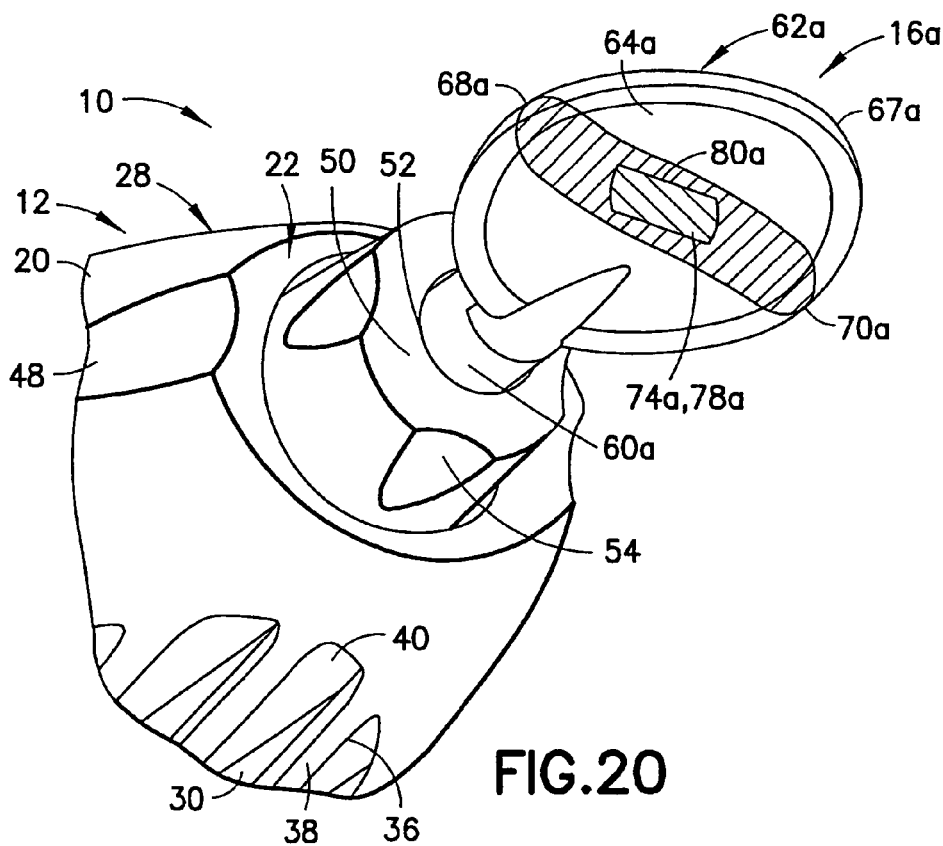
FIG. 20 is a perspective and partial cross-sectional view of the lancet device of FIG. 17 showing a cross-section of the second embodiment of the tab member.
Figure 21:
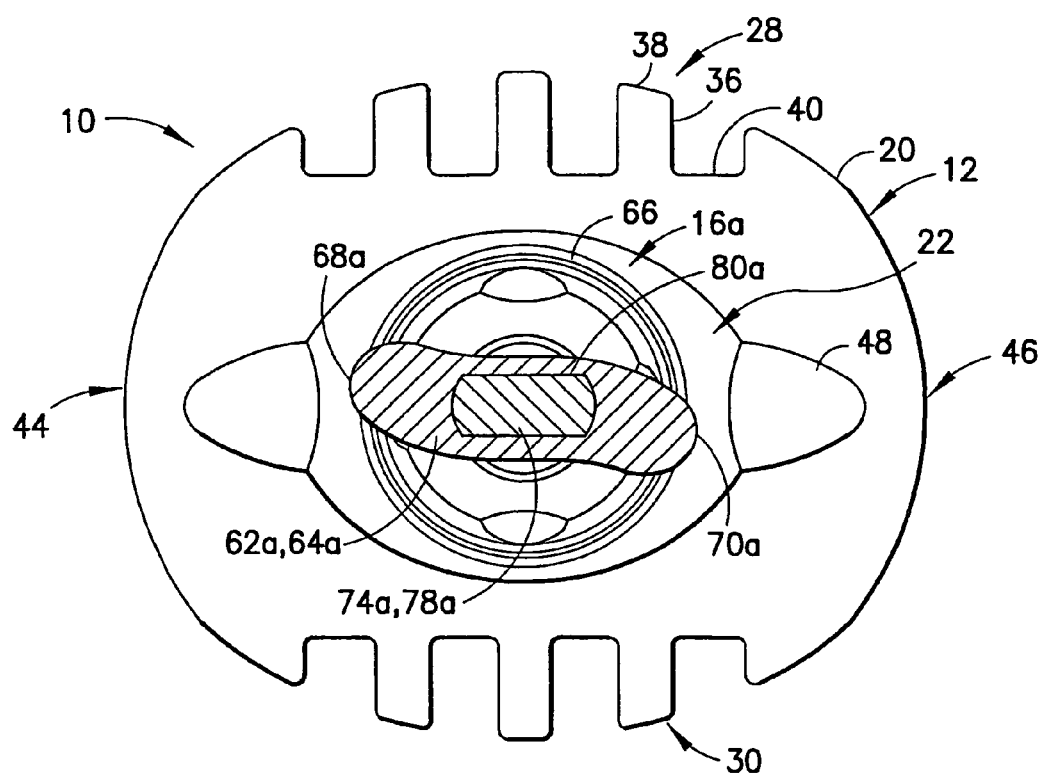
FIG. 21 is a distal end view and partial cross-sectional view of the lancet device of FIG. 17 showing a cross-section of the second embodiment of the tab member.
Figure 22:
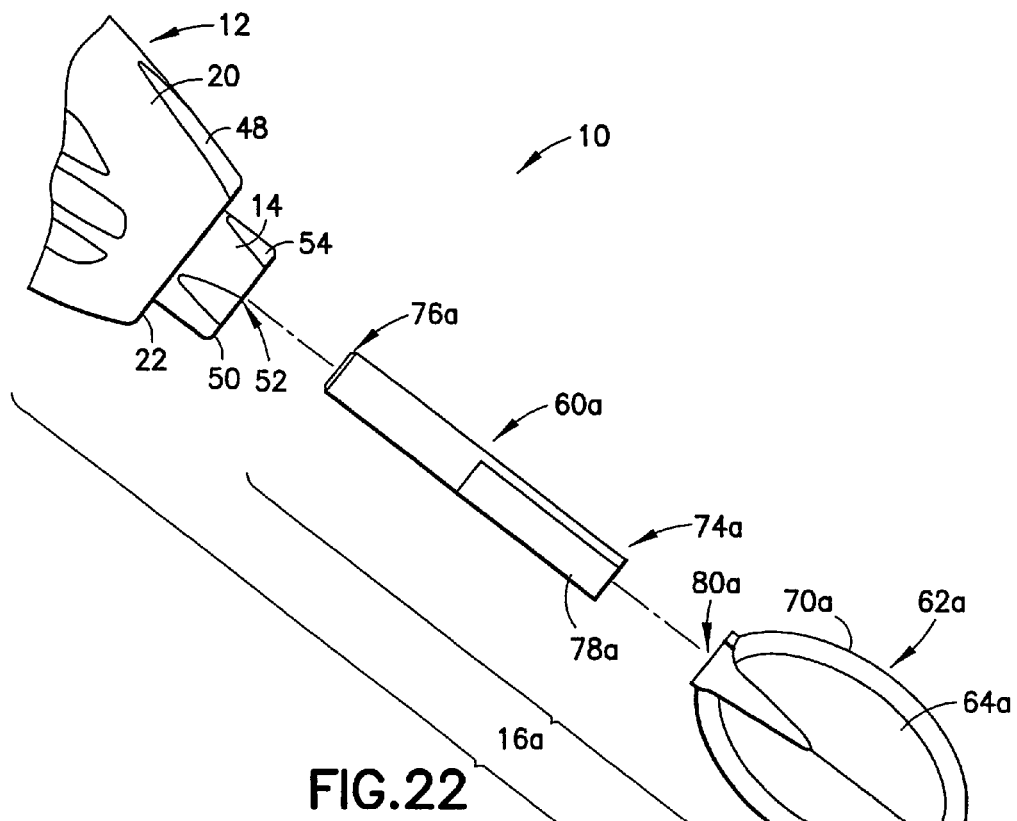
FIG. 22 is an exploded perspective view of the lancet device and tab member of FIG. 17 showing separable components of the second embodiment of the tab member.
Figure 23:
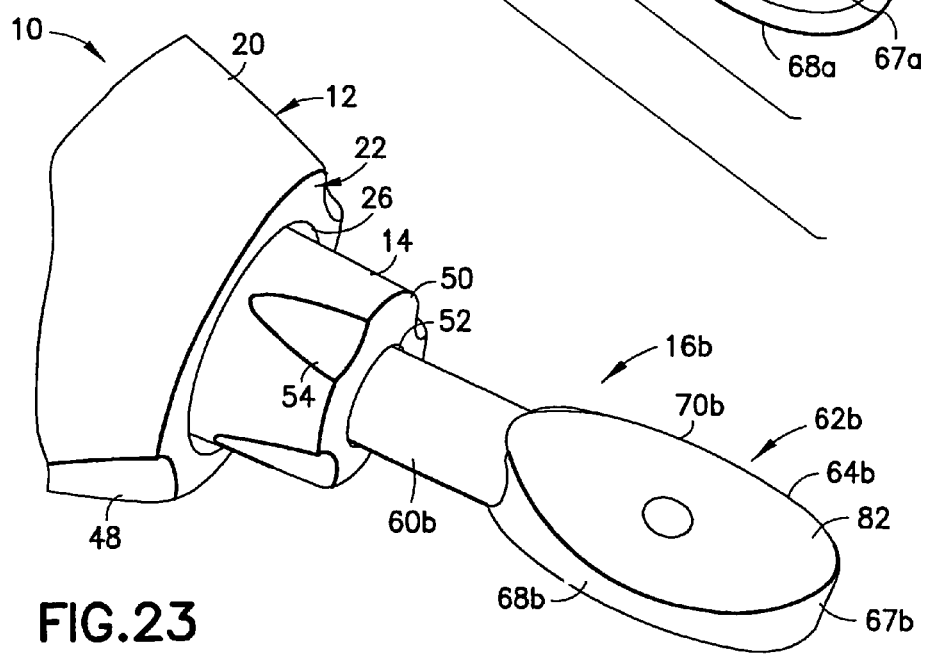
FIG. 23 is a perspective view of the distal end of the lancet device with a third embodiment of the tab member.
Figure 24:
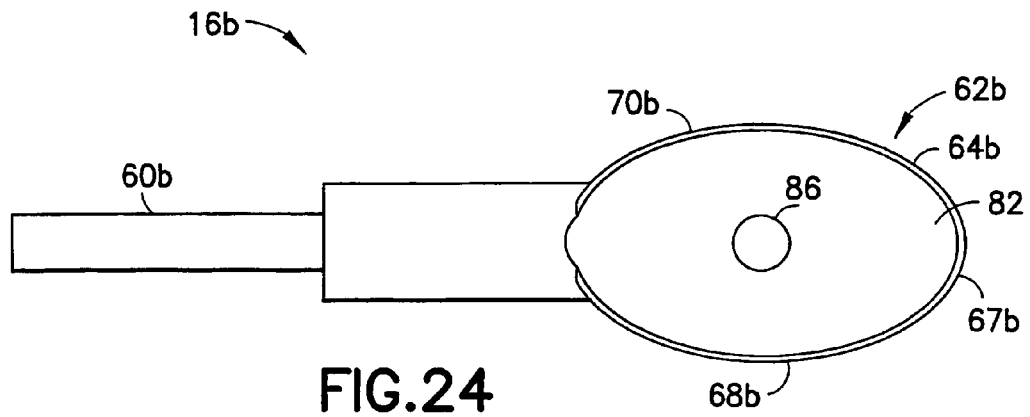
FIG. 24 is a plan view of the tab member shown in FIG. 23.
Figure 25:
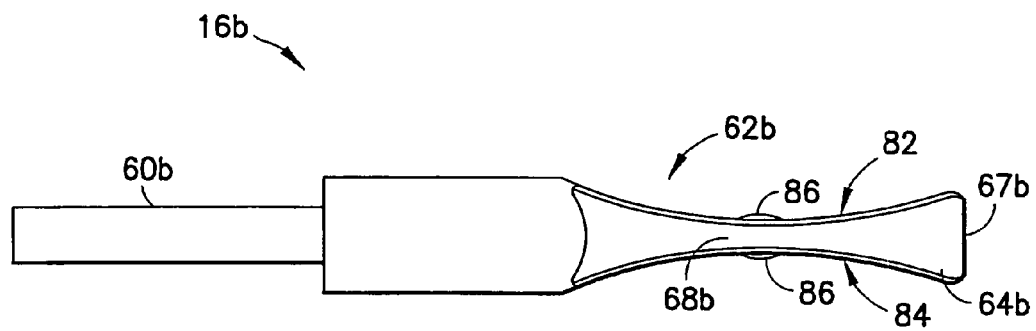
FIG. 25 is a side elevational view of the tab member of FIG. 24.
Figure 26:
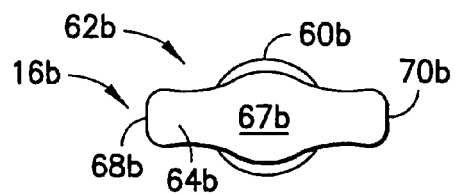
FIG. 26 is a distal end view of the tab member of FIG. 24.
Figure 29:
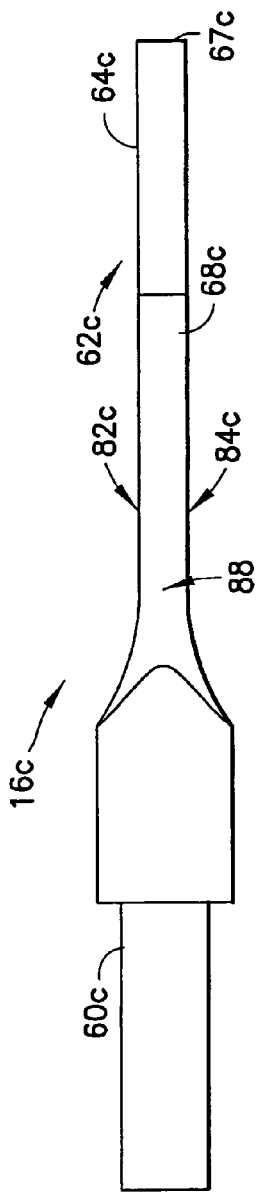
FIG. 29 is a side elevational view of the tab member of FIG. 27.
Figure 30:
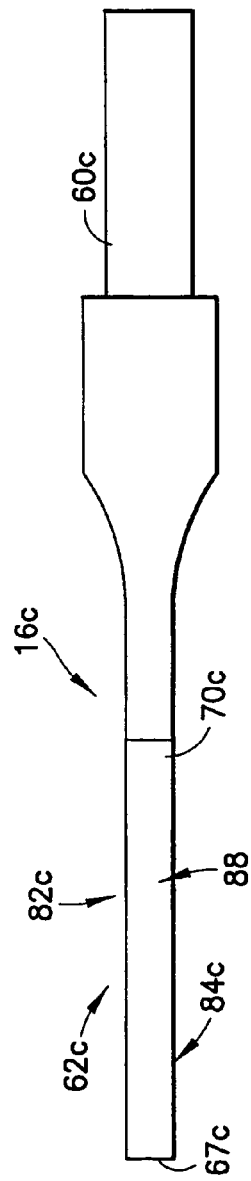
FIG. 30 is an opposite side elevational view of the tab member of FIG. 27.
Figure 31:
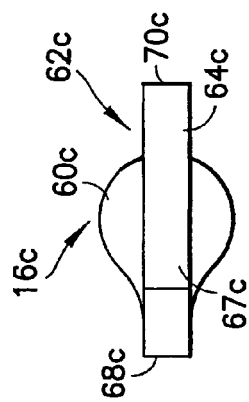
FIG. 31 is a distal end view of the tab member of FIG. 27.
Figure 34:
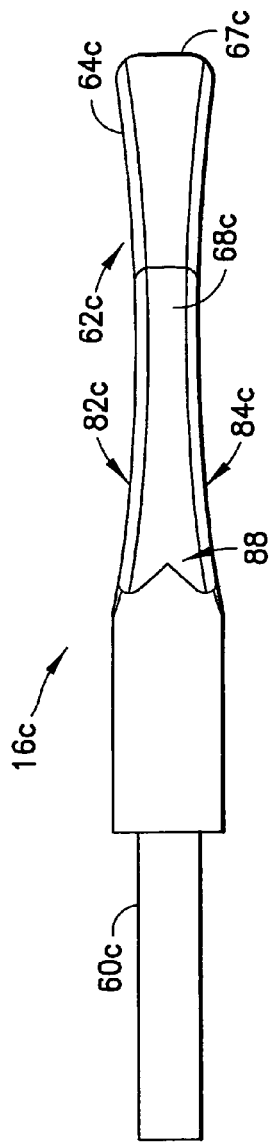
FIG. 34 is a side elevational view of the tab member of FIG. 32.
Figure 35:
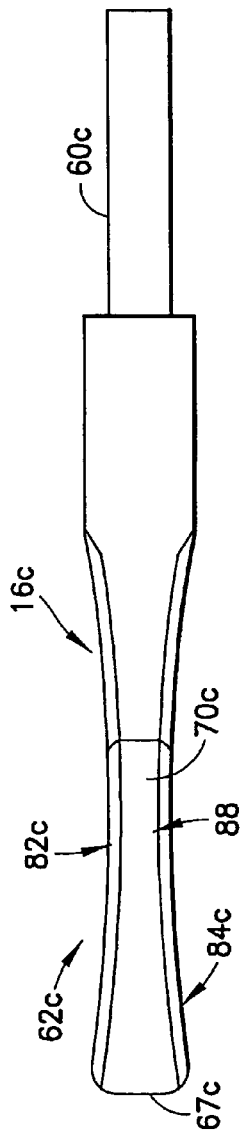
FIG. 35 is an opposite side elevational view of the tab member of FIG. 32.
Figure 36:
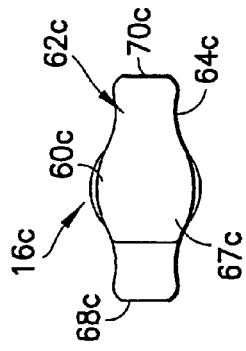
FIG. 36 is a distal end view of the tab member of FIG. 32.
Figure 43:
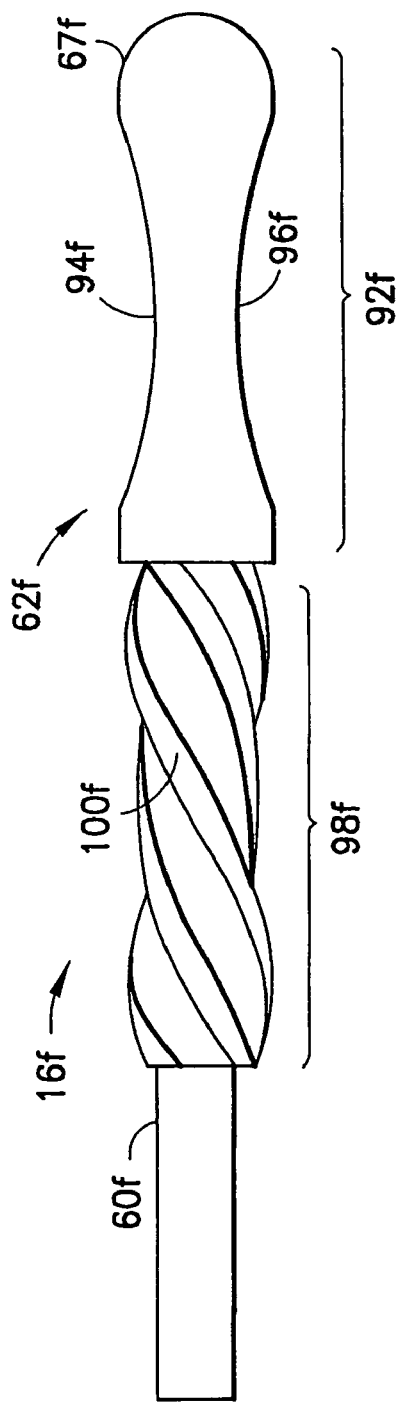
FIG. 43 is a side elevational view of the tab member of FIG. 41
Figure 44:
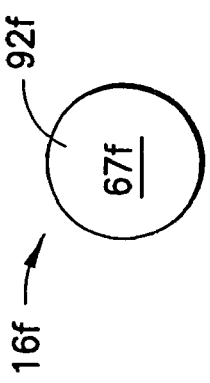
FIG. 44 is a distal end view of the tab member of FIG. 41.
Figure 47:
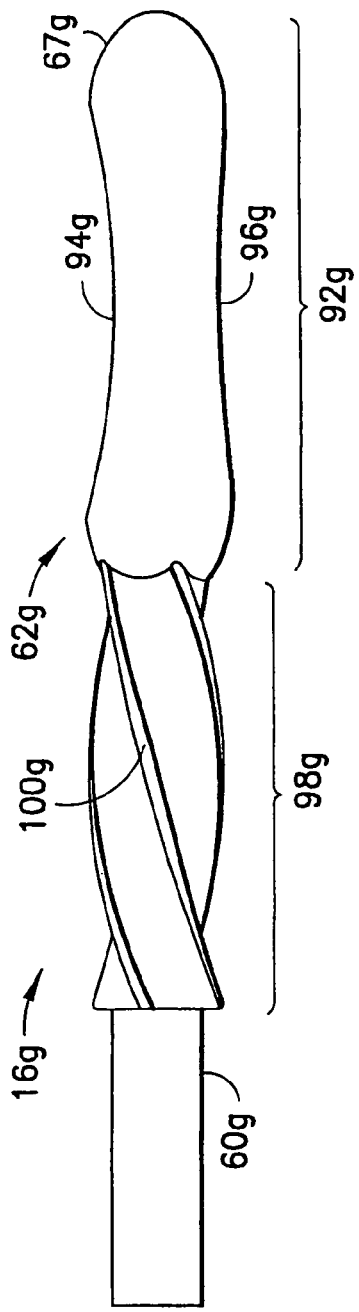
FIG. 47 is a side elevational view of the tab member of FIG. 45.
Figure 48:
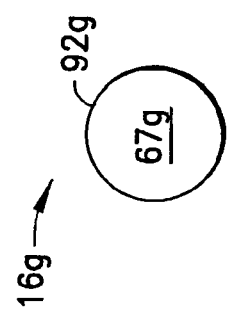
FIG. 48 is a distal end view of the tab member of FIG. 45.

The tab member 16a still includes the post portion 60a and the distal portion 62a, with the post portion 60a and distal portion 62a separable from each other in the manner discussed previously in connection with the first embodiment of the tab member 16. As shown in FIGS. 20 and 21, the paddle-shaped member 64a also exhibits a contoured profile formed or defined by oppositely curved edges 68a, 70a of the paddle-shaped member 64a.

FIGS. 23-26 show a third embodiment of the tab member 16b. The third embodiment of the tab member 16b is configured in substantially the same manner as the second embodiment of the tab member 16a and varies generally in the shape and formation of the paddle-shaped member 64b. The paddle-shaped member 64b is also generally oval-shaped, prolate, or elliptical in this embodiment. However, the opposed top and bottom sides 82, 84 of the paddle-shaped member 64b are contoured in a slightly different manner than the previously discussed embodiments of the tab member 16, 16a. In this embodiment, the opposed edges 68b, 70b of the paddle-shaped member 64b are not oppositely curved, so the paddle-shaped member 64b exhibits a generally bilateral symmetrical cross-section as will be apparent when viewing FIG. 26. The contoured sides 82, 84 are formed generally as finger grip indentations in a similar to the side finger grip indentations 32 in the housing body 20. The contoured sides 82, 84 may define a hyperbolic, parabolic, semicircular shape. The finger grip indentations formed by the contoured sides 82, 84 are generally concave, for example hyperbolic shaped, to naturally fit the fingertips of the user. The contoured sides 82, 84 of the paddle-shaped member 64b may each include one or more raised finger grip tabs 86 for improving the frictional characteristics between the paddle-shaped member 64b and the user's fingertips. The post portion 60b may be detachably connected to the distal portion 62b in an analogous manner to the previously discussed embodiments of the tab member 16, 16a.

FIGS. 27-31 show a fourth embodiment of the tab member 16c. The fourth embodiment of the tab member 16c is configured in substantially the same manner as the second and third embodiments of the tab member 16a, 16b, and again varies primarily in the shape and formation of the paddle-shaped member 64c. In this embodiment, the paddle-shaped member 64c is generally non-symmetrical in plan view, and the opposed edges 68c, 70c of the paddle-shaped member 64b are not oppositely curved. However, the opposed edges 68c, 70c define opposed longitudinal curved portions or bulge portions 88, as best shown in FIG. 28, which causes the overall the shape of the paddle-shaped member 64c to be non-symmetrical. The opposed curved portions 88 are generally hyperbolic or elliptical-shaped (i.e., concave) as shown in FIGS. 27 and 28. In contrast to the previously discussed embodiments, the opposed sides 82c, 84c of the paddle-shaped member 64c are not contoured and are formed as generally planar surfaces. The opposed sides 82c, 84c each define one or more shaped indentations 90 therein. As shown in FIG. 28, the indentations 90 may have any suitable shape such as triangular (i.e., polygonal shaped). Other suitable shapes include circular, semicircular, oval, or non-symmetrical shapes. The shaped indentations 90 generally take the place of the raised finger grip tabs 86 provided on the paddle-shaped member 64b discussed previously. The post portion 60c may be detachably connected to the distal portion 62c in an analogous manner to the previous embodiments of the tab member 16, 16a, 16b.

FIGS. 32-36 show a fifth embodiment of the tab member 16d. This embodiment is substantially similar to the tab member 16c discussed immediately above. In this embodiment, the paddle-shaped member 64d is also generally non-symmetrical in plan view, and the opposed edges 68d, 70d of the paddle-shaped member 64d are not oppositely curved. However, the opposed edges 68d, 70d define opposed longitudinal curved portions 88d, as shown in FIGS. 32 and 33, in a similar manner to the tab member 16c shown in FIGS. 27-31. In contrast to the immediately preceding embodiment of the tab member 16c, the opposed sides 82d, 84d of the paddle-shaped member 64d are contoured in a manner similar to the embodiment of the tab member 16b shown in FIGS. 23-36 and discussed previously. The contoured sides 82d, 84d are formed generally as finger grip indentations in a similar to the side finger grip indentations 32 in the housing body 20. The finger grip indentations formed by the contoured sides 82d, 84d are generally concave to naturally fit the fingertips of the user. The contoured sides 82d, 84d of the paddle-shaped member 64b may each include one or more raised finger grip tabs (not shown), which may be similar to the raised finger grip tabs 86 shown in FIGS. 23-25, for improving the frictional characteristics between the paddle-shaped member 64d and the user's fingertips. The post portion 60d may be detachably connected to the distal portion 62d in an analogous manner to the previous embodiments of the tab member 16, 16a, 16b, 16c.

FIGS. 37-40 show a sixth embodiment of the tab member 16e. In this embodiment, the tab member 16e has a generally cylindrical shape over its length, and only reduces in cross-section at the post portion 60e. The distal portion 62e is no longer formed with a paddle-shaped member and is also generally cylindrical-shaped over its length. In this embodiment, the distal portion 62e includes a distal gripping tip 92 formed with opposed finger grip indentations 94, 96 for grasping by the user. The finger grip indentations 94, 96 are formed similar to the side finger grip indentations 32 in the housing body 20, therefore having a hyperbolic or elliptical shape (i.e., concave) as shown in FIG. 39. The finger grip indentations 94, 96 are generally concave to naturally fit the fingertips of the user. The distal portion 62e of the tab member 16 further defines an intermediate portion or area 98 disposed between the post portion 60e and the finger grip indentations 94, 96. The intermediate portion 98 defines a helical texture 100 thereon. The helical texture may be referred to as a helical sweep, helical spline, or optionally represented as external threads or a helical spring. The helical texture 100 extends generally from an area just below the finger grip indentations 94, 96 on the gripping tip 92 to the post portion 60e. The helical texture 100 provides a visual and tactile cue to the user to indicate to the user that the tab member 16e should be rotated to remove the tab member 16e from association with the actuating mechanism and/or puncturing element disposed within the housing 12. The helical texture 100 could be used to indicate to the user that the puncture tip enclosed by the tab member 16e is likely to be a pointed puncturing element such as a needle rather than a blade-type cutting element having a cutting edge. The intermediate portion 16e may include a transition band 102 that smoothly transitions the helical texture 100 to a smooth texture provided on the distal gripping tip 92.

FIGS. 41-44 show a seventh embodiment of the tab member 16f. The tab member 16f is formed substantially identically to the tab member 16e shown in FIGS. 37-40 discussed immediately above with a slight variation in the way the helical texture 110f on the intermediate portion 98f is formed. The helical texture 100f is tapered further in the longitudinal direction along the intermediate portion 98f when compared to the helical texture 100 on the intermediate portion 98 shown in FIGS. 37-41. Additionally, the intermediate portion 98f may omit the transition band 102 discussed previously in connection with FIGS. 37-41, and connect directly or abruptly to the gripping tip 92f as illustrated.

FIGS. 45-48 show an eighth and final embodiment of the tab member 16g. The tab member 16g is substantially identical to the tab member 16f discussed immediately above, with a few minor changes. First, the tab member 16g includes one or more raised finger grip tabs 104 formed on each of the finger grip indentations 94g, 96g. The finger grip indentations 94g, 96g resemble hyperbolic or elliptical (i.e., concave) surfaces. Additionally, the helical texture 100g on the intermediate portion 98g tapers more smoothly from the gripping tip 92g than in the tab member 16f. Finally, the rounded distal end 67g of the distal portion 62g is slightly more pointed (i.e., less rounded) than the corresponding distal end 67f on the distal portion 62f of the tab member 16f discussed hereinabove.

Figure 49:
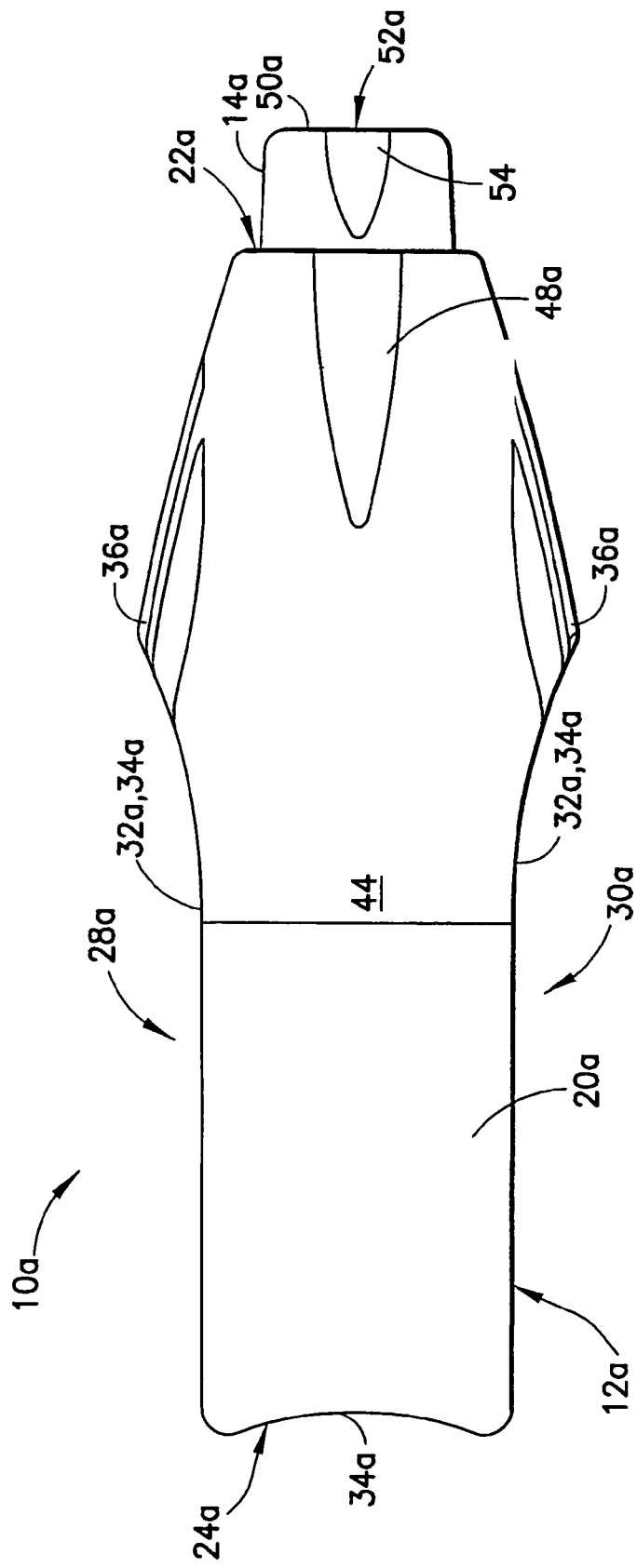
FIG. 49 is a side elevational view of an alternative embodiment of the lancet device in accordance with the present invention.
Figure 50:
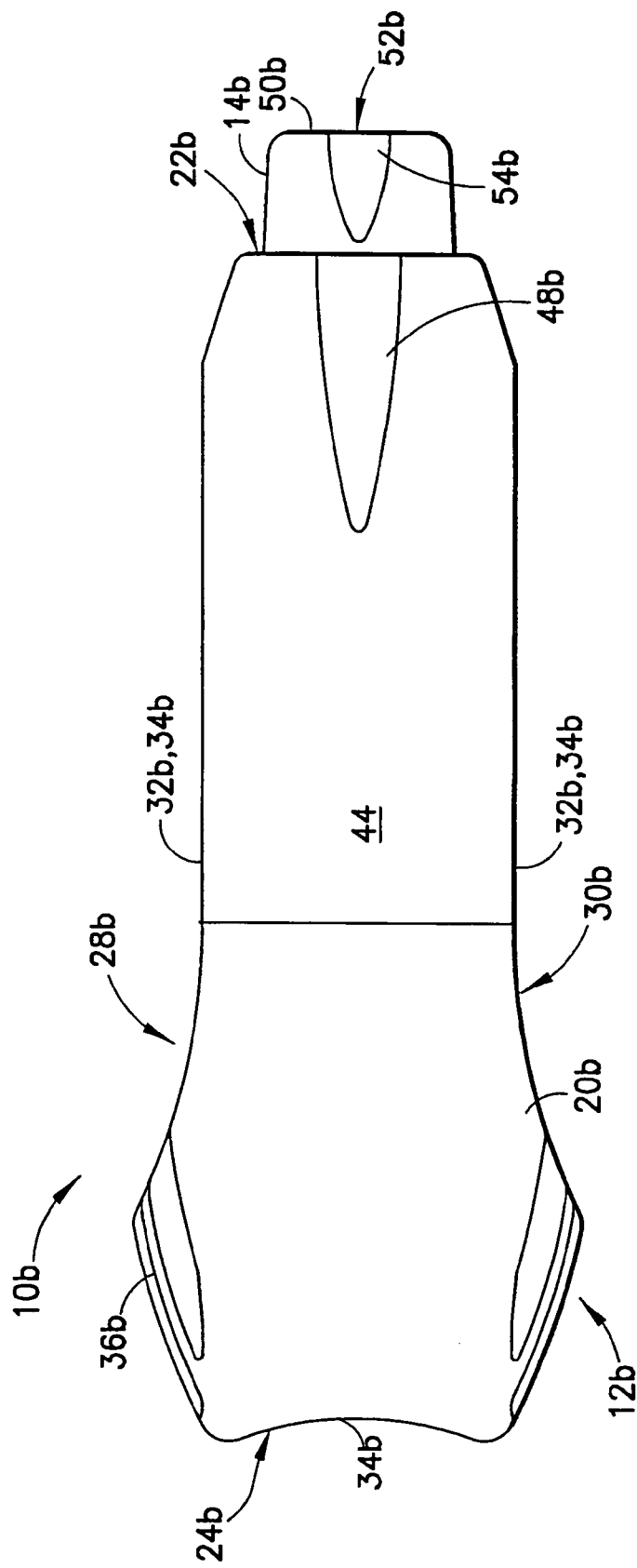
FIG. 50 is a side elevational view of another alternative embodiment of the lancet device in accordance with the present invention.

FIGS. 49 and 50 show two alternative embodiments of the lancet device 10a, 10b in accordance with the present invention. The lancet devices 10a, 10b differ from the lancet device 10 described previously primarily in the formation of the finger grip indentations 32a, 32b. In FIG. 49, the fingergrip indentations 32a in the opposed sides 28a, 30a of the housing body 20a are still generally in the form of concave-shaped depressions or recesses for accommodating the fingertips of the user of the lancet device 10. However, the fingergrip indentations 32a now transition to a generally cylindrical portion of the housing body 20a transitioning from the fingergrip indentations 32a to the proximal end 24a of the housing body 20a. The finger grip indentations 32a may further be in the form of hyperbolic, parabolic, or semicircular shaped indentations, recesses, or depressions in the opposed sides 28a, 30a of the housing body 20a as described previously. In FIG. 50, the fingergrip indentations 32b transition to a generally cylindrical portion of the housing body 20b extending from the fingergrip indentations 32b to the distal end 22b of the housing body 20b, or in the opposite manner from that depicted in FIG. 49.

While the present invention was described with reference to preferred embodiments of the lancet device and sterile tab member thereof, those skilled in the art may make modifications and alterations to the present invention without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

The invention claimed is:

1. A lancet device, comprising:
   a housing comprising opposing lateral sides extending between a forward end and a rearward end, the housing further comprising a plurality of longitudinal ribs extending along a portion of at least one of the opposing lateral sides, the plurality of longitudinal ribs forming a finger grip on the at least one of the opposing lateral sides; and
   a shield coaxially and movably associated with the housing such that axial pressure applied by the user against the finger grip moves the housing and the shield with respect to each other from a first position in which the shield extends outwardly from the forward end of the housing to a second position in which the shield is at least partially moved within the housing.

2. The lancet device of claim 1, wherein the longitudinal ribs extend along a portion of both of the opposing lateral sides of the housing forming finger grips on both of the opposing lateral sides.

3. The lancet device of claim 1, wherein a portion of each of the longitudinal ribs is contoured to form the finger grip as a generally concave surface.

4. The lancet device of claim 3, wherein another portion of the longitudinal ribs is contoured to form a generally convex surface.

5. The lancet device of claim 4, wherein the longitudinal ribs are contoured to generally form a forward convex surface at a portion of the opposing lateral side adjacent the forward end and a rearward convex surface at a portion of the opposing lateral side adjacent the rearward end of the housing, with the generally concave surface formed between the forward and the rearward convex surfaces.

6. The lancet device of claim 5, wherein the longitudinal ribs forming the forward and the rearward convex surfaces are aligned through the concave surface to form the finger grip as an indentation on at least of the opposing lateral sides of the housing.

7. The lancet device of claim 5, wherein the longitudinal ribs form a generally oval concave surface.

8. The lancet device of claim 1, wherein the housing further comprises a finger grip indentation formed on the rearward end of the housing for accommodating a user's finger during use of the lancet device.

9. The lancet device of claim 8, wherein the finger grip indentation formed on the rearward end of the housing is concave.

10. The lancet device of claim 1, wherein the shield defines a plurality of peripherally spaced indentations for visually indicating an alignment position of a puncturing element disposed within the housing and/or the shield.

11. A lancet device, comprising:
    a housing extending between a forward end and a rearward end;
    a shield extending coaxially through the forward end of the housing and movably associated with the housing;
    a lancet assembly disposed in the housing and adapted to extend through an opening in a forward end of the shield upon movement of the shield with respect to the housing; and
    a removable tab member having an inner portion maintaining sterility of a lance tip of the lancet assembly and an outer portion enclosing the opening in the forward end of the shield and adapted to maintain the shield and the housing from axially moving with respect to each other.

12. The lancet device of claim 11, wherein the inner portion of the tab member comprises a post substantially enclosing the lance tip, and the outer portion of the tab member further comprises a grip portion adapted to be grasped by the user.

13. The lancet device of claim 12, wherein the outer portion of the tab member comprises a depending skirt formed to engage an external surface of the forward end of the shield extending from the forward end of the housing.

14. The lancet device of claim 13, wherein the depending skirt includes structure for cam-like engagement with the forward end of the housing to facilitate removal of the tab member.

15. The lancet device of claim 12, wherein the grip portion comprises a paddle-shaped member for grasping by the user.

16. The lancet device of claim 15, wherein opposed longitudinal edges of the paddle-shaped member are oppositely curved such that opposed sides of the paddle-shaped member define contouring to indicate to a user a rotational direction for rotating the tab member to assist in removing the tab member.

17. The lancet device of claim 16, wherein a transverse cross-section through the paddle-shaped member defines a general wave or S-shape.

18. The lancet device of claim 15, wherein the paddle-shaped member is generally oval-shaped.

19. The lancet device of claim 15, wherein opposed sides of the paddle-shaped member are concave.

20. The lancet device of claim 15, wherein opposed sides of the paddle-shaped member include at least one raised grip tab thereon.

21. The lancet device of claim 15, wherein opposed edges of the paddle-shaped member define opposed longitudinal curved portions.

22. The lancet device of claim 21, wherein the opposed longitudinal curved portions are generally elliptical shaped.

23. The lancet device of claim 21, wherein at least one shaped indentation is defined in at least one side of the paddle-shaped member.

24. The lancet device of claim 23, wherein the shaped indentation is polygonal shaped.

25. The lancet device of claim 12, wherein the grip portion defines opposed finger grip indentations for grasping by the user.

26. The lancet device of claim 25, wherein the finger grip indentations are concave.

27. The lancet device of claim 25, wherein the grip portion comprises an intermediate portion adjacent the post portion and grip portion, the intermediate portion defining a helical texture.

28. The lancet device of claim 25, wherein the finger grip indentations each include at least one raised grip tab.

29. The lancet device of claim 12, wherein the grip portion is detachable from the post.

* * * * *